(12) United States Patent
Endo et al.

(10) Patent No.: US 9,428,606 B2
(45) Date of Patent: Aug. 30, 2016

(54) POLYFUNCTIONAL EPOXY COMPOUND

(75) Inventors: Yuki Endo, Funabashi (JP); Toshiaki Takeyama, Funabashi (JP); Sayoko Yanagisawa, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 448 days.

(21) Appl. No.: 13/885,298

(22) PCT Filed: Nov. 14, 2011

(86) PCT No.: PCT/JP2011/076194
§ 371 (c)(1),
(2), (4) Date: Jun. 21, 2013

(87) PCT Pub. No.: WO2012/067071
PCT Pub. Date: May 24, 2012

(65) Prior Publication Data
US 2013/0274433 A1 Oct. 17, 2013

(30) Foreign Application Priority Data
Nov. 15, 2010 (JP) ................. 2010-254768

(51) Int. Cl.
| | | |
|---|---|---|
| C07D 303/16 | (2006.01) | |
| C07D 303/44 | (2006.01) | |
| C08G 59/02 | (2006.01) | |
| C08G 59/32 | (2006.01) | |
| H01L 23/29 | (2006.01) | |
| H05K 3/28 | (2006.01) | |
| H05K 3/46 | (2006.01) | |

(52) U.S. Cl.
CPC ............ C08G 59/02 (2013.01); C07D 303/16 (2013.01); C07D 303/44 (2013.01); C08G 59/027 (2013.01); C08G 59/32 (2013.01); H01L 23/293 (2013.01); *H01L 2924/0002* (2013.01); *H05K 3/285* (2013.01); *H05K 3/287* (2013.01); *H05K 3/4676* (2013.01)

(58) Field of Classification Search
CPC .. C07D 303/16; C07D 303/44; C08G 59/02; C08G 59/32
See application file for complete search history.

(56) References Cited

U.S. PATENT DOCUMENTS

| | | | | |
|---|---|---|---|---|
| 3,122,568 A | * | 2/1964 | Lynn | .................... C07D 303/16 524/109 |
| 3,442,752 A | | 5/1969 | Sandler et al. | |
| 3,565,922 A | | 2/1971 | Rudy et al. | |
| 4,865,963 A | * | 9/1989 | Furutachi | ............. C07D 487/04 430/386 |
| 5,169,965 A | | 12/1992 | Fujiwa et al. | |
| 5,198,509 A | | 3/1993 | Fujiwa et al. | |
| 5,338,879 A | | 8/1994 | Fujiwa et al. | |
| 6,433,084 B1 | | 8/2002 | Gottis | |
| 7,247,684 B2 | * | 7/2007 | Lopez | ................ C08G 59/5006 428/457 |
| 2004/0180981 A1 | | 9/2004 | Lopez et al. | |
| 2010/0093947 A1 | | 4/2010 | Okada et al. | |

FOREIGN PATENT DOCUMENTS

| | | | |
|---|---|---|---|
| JP | A-50-10893 | | 2/1975 |
| JP | A-50-12050 | | 2/1975 |
| JP | A-51-125318 | | 11/1976 |
| JP | A-52-71402 | | 6/1977 |
| JP | A-60-69156 | | 4/1985 |
| JP | A-1-170655 | | 7/1989 |
| JP | A-4-69360 | | 3/1992 |
| JP | A-2006-274190 | | 10/2006 |
| JP | 2008-101199 | * | 5/2008 |
| JP | A-2008-101199 | | 5/2008 |
| JP | A-2008-274159 | | 11/2008 |

OTHER PUBLICATIONS

International Search Report issued in International Patent Application No. PCT/JP2011/076194 mailed Feb. 14, 2012.
Written Opinon of the International Searching Authority issued in International Patent Application No. PCT/JP2011/076194 mailed Feb. 14, 2012.

* cited by examiner

Primary Examiner — Valerie Rodriguez-Garcia
(74) Attorney, Agent, or Firm — Oliff PLC

(57) ABSTRACT

There is provided an epoxy resin composition having low viscosity and a high cationic curing property. An epoxy compound of Formula (1):

Formula (I)

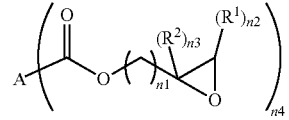

(in Formula (1), A is an (n4)-valent $C_{4-20}$ linear hydrocarbon group optionally containing an epoxy group, an (n4)-valent $C_{4-20}$ cyclic hydrocarbon group optionally containing an epoxy group, or an (n4)-valent group of a combination of the linear hydrocarbon group and the cyclic hydrocarbon group; $R^1$ and $R^2$ are each independently a hydrogen atom or a $C_{1-10}$ alkyl group; n1 is an integer of 2 to 6; n2 is an integer of 2; n3 is an integer of 1; and n4 is an integer of 3 to 8). For example, A is an (n4)-valent organic group formed by removing (n4) hydrogen atoms from butane, pentane, or hexane, or an (n4)-valent organic group formed by removing (n4) hydrogen atoms from cyclobutane, cyclopentane, cyclohexane, epoxycyclohexane, alkyl-substituted epoxycyclohexane, bicycloheptene, or bicyclooctene.

10 Claims, No Drawings

POLYFUNCTIONAL EPOXY COMPOUND

TECHNICAL FIELD

The present invention relates to a photocurable or thermocurable epoxy resin composition. More particularly, the present invention relates to a photocurable or thermocurable epoxy resin composition (a resin composition for electronic materials and optical materials) that is useful for obtaining a cured product having excellent properties such as high adhesion to a substrate, high transparency (transparency to visible light), a hard-coat property, and high heat resistance and the cured product thereof (a cured composite).

BACKGROUND ART

Epoxy resins have been widely used in electronic material fields as epoxy resin compositions combined with curing agents. Properties such as the high adhesion to a substrate, the hard-coat property, the high heat resistance, and the high transparency for visible light are required for a molding material in applications to, among such electronic material fields, for example, a high refractive index layer of an anti-refractive coating (such as an anti-refractive coating for a liquid-crystal display), an optical thin film (such as a reflecting plate), a sealant for electronic parts, a printed circuit board, and a material for an interlayer insulation film (such as a material for an interlayer insulation film for a buildup printed circuit board).

On the other hand, many studies have been carried out these days on epoxy resin compositions in which an epoxy compound is combined with a photo or thermal acid generator because the epoxy resin composition does not need a solvent and the epoxy compound can be singly cured. Particularly, photo-cationic curing by ultraviolet ray is extremely excellent in that the curing does not need a large oven for curing and an amount of energy consumption is small.

An alicyclic epoxy compound in which only an alicyclic structure has an epoxy group is widely used because it is highly reactive to cationic curing using light. However, the cured product tends to be hard and brittle because its structure is rigid.

A lactone-modified multifunctional alicyclic epoxy compound and an epoxy resin composition using the epoxy compound and a method of producing the same are disclosed (refer to Patent Document 1).

On the other hand, it has been generally considered that a glycidyl ester-based epoxy compound is not suitable for cationic curing because such an epoxy compound has low reactivity with acid generators and needs much reaction time.

As the multifunctional epoxy compounds having glycidyl ester groups, epoxy resin compositions using cyclobutanetetracarboxylic acid tetraglycidyl ester, cyclopentanetetracarboxylic acid tetraglycidyl ester, and cyclohexanetricarboxylic acid triglycidyl ester are disclosed (refer to Patent Documents 2 and 3).

A carboxy group-containing resin employing, as a crosslinkable compound, an epoxyalkyl ester of a cyclohexanedicarboxylic acid having an epoxy group is disclosed (refer to Patent Document 4).

Patent Document 1: Japanese Patent Application Publication No. 4-069360 (JP 4-069360 A)

Patent Document 2: Japanese Patent Application Publication No. 50-010893 (JP 50-010893 A)

Patent Document 3: Japanese Patent Application Publication No. 2006-274190 (JP 2006-274190 A) Patent Document 4: U.S. Pat. No. 3,565,922 Specification

SUMMARY OF THE INVENTION

Problem to be Solved by the Invention

As a result of intensive studies, the inventors of the present invention have found that a cationic curing property is provided to a multifunctional epoxy compound that includes a $C_{4-20}$ linear hydrocarbon group optionally including an epoxy group, a $C_{4-20}$ cyclic hydrocarbon group optionally including an epoxy group, or an organic group of a combination of them as a skeleton, in which the skeleton has a plurality of side chains, the side chains are epoxy groups bonded through ester bonds and alkylene groups, and the multifunctional epoxy compound includes such a plurality of epoxy groups in one molecule. Therefore, the present invention is to provide the epoxy compound, and a curable composition made by using the epoxy compound and having low viscosity and a high cationic curing property. A cured product obtained from this curable composition has high toughness.

Means for Solving the Problem

The present invention includes the following aspects. As a first aspect, an epoxy compound of Formula (1):

Formula (I)

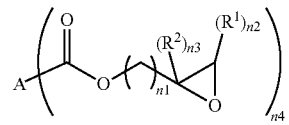

(in Formula (1), A is an (n4)-valent $C_{4-20}$ linear hydrocarbon group optionally containing an epoxy group, an (n4)-valent $C_{4-20}$ cyclic hydrocarbon group optionally containing an epoxy group, or an (n4)-valent group of a combination of the linear hydrocarbon group and the cyclic hydrocarbon group; $R^1$ and $R^2$ are each independently a hydrogen atom or a $C_{1-10}$ alkyl group; n1 is an integer of 2 to 6; n2 is an integer of 2; n3 is an integer of 1; and n4 is an integer of 3 to 8);

as a second aspect, the epoxy compound according to the first aspect, in which A is an (n4)-valent organic group formed by removing (n4) hydrogen atoms from butane, pentane, or hexane;

as a third aspect; the epoxy compound according to the first aspect, in which A is an (n4)-valent organic group formed by removing (n4) hydrogen atoms from cyclobutane, cyclopentane, cyclohexane, epoxycyclohexane, alkyl-substituted epoxycyclohexane, bicycloheptene, or bicyclooctene;

as a fourth aspect, a curable composition including the epoxy compound as described in any one of the first aspect to the third aspect and a curing agent;

as a fifth aspect, the curable composition according to the fourth aspect, in which the curing agent is at least one selected from the group consisting of an acid anhydride, amines, a phenol resin, a polyamide resin, imidazoles, and a polymercaptan;

as a sixth aspect, the curable composition according to the fourth aspect or the fifth aspect, in which the curing agent is contained in a ratio of 0.5 equivalents to 1.5 equivalents relative to 1 equivalent of the epoxy group in the epoxy compound;

as a seventh aspect, a curable composition including the epoxy compound as described in any one of the first aspect to the third aspect and an acid generator;

as a eighth aspect, the curable composition according to the seventh aspect, in which the acid generator is a photo acid generator or a thermal acid generator;

as a ninth aspect, the curable composition according to the seventh aspect, in which the acid generator is an onium salt;

as a tenth aspect, the curable composition according to the seventh aspect, in which the acid generator is a sulfonium salt compound or an iodonium salt compound; and as an eleventh aspect, the curable composition according to any one of the seventh aspect to the tenth aspect, in which the acid generator is contained in a ratio of 0.1% by mass to 20% by mass per mass of the epoxy compound.

EFFECTS OF THE INVENTION

In the epoxy compound having an epoxy ring bonded to an organic group being the skeleton through an ester bond and an alkylene group, the longer the alkylene group, the higher the degree of freedom of the epoxy ring, and every epoxy ring can contribute to reaction. This enhances a cationic curing property. Thus, in the curable resin composition of the present invention, due to its rapid curing rate, an amount of an acid generator to be added can be reduced and a weak acid-based acid generator can be used. Here, the reduction in the amount of an acid generator used is important for corrosion inhibition of metals because active acid species derived from the acid generator may remain after UV irradiation. The curable resin composition of the present invention can be cured into a thick film due to the rapid curing rate.

In the present invention, photo curing of the curable composition containing the epoxy compound and a photo acid generator can form a cured product or a cured coating film that satisfy both excellent mechanical properties and excellent optical properties. Furthermore, a longer alkylene group of the epoxy compound provides higher toughness of the cured product or the cured coating film.

The curable composition of the present invention may contain an epoxy compound and a curing agent (for example, amines or acid anhydrides), and further, optionally a curing aid.

In the present invention, an epoxy compound is cured by light or cured by heating using a photo acid generator or a thermal acid generator. Consequently, the curable composition of the present invention has excellent storage stability by using a photo acid generator or a thermal acid generator because a typical curing agent of an epoxy compound (for example, amines or acid anhydrides) is not used or, if used, a content of the curing agent is extremely low.

The curable composition of the present invention is photo-cured with UV radiation and thus is applicable for production of a material (a material for equipment) that is heat-sensitive.

The viscosity of the epoxy compound of the present invention is low. Thus, the curable resin composition of the present invention using the epoxy compound of the present invention has an excellent filling property.

The cured product formed from the curable composition of the present invention has characteristics such as low viscosity and rapid curing and is applicable for coating and adhesion of electronic parts, optical parts, and precision mechanism parts.

MODES FOR CARRYING OUT THE INVENTION

The present invention is the epoxy compound of Formula (1). In Formula (1), A is an (n4)-valent $C_{4-20}$ linear hydrocarbon group optionally containing an epoxy group, an (n4)-valent $C_{4-20}$ cyclic hydrocarbon group optionally containing an epoxy group, or an (n4)-valent group of a combination of them; $R^1$ and $R^2$ are each independently a hydrogen atom or a $C_{1-10}$ alkyl group: n1 is an integer of 2 to 6; n2 is an integer of 2; n3 is an integer of 1; and n4 is an integer of 3 to 8.

When A of Formula (1) is a linear hydrocarbon group, examples of A include (n4)-valent organic groups formed by removing (n4) hydrogen atoms from butane, pentane, or hexane.

When A of Formula (1) is a cyclic hydrocarbon group, examples of A include (n4)-valent organic groups formed by removing (n4) hydrogen atoms from cyclobutane, cyclopentane, or cyclohexane, epoxycyclohexane, alkyl-substituted epoxycyclohexane, bicycloheptene, and bicyclooctene.

In Formula (1), $R^1$ and $R^2$ are each independently a hydrogen atom or a $C_{1-10}$ alkyl group.

Examples of the $C_{1-10}$ alkyl group include a methyl group, an ethyl group, an n-propyl group, an i-propyl group, a cyclopropyl group, an n-butyl group, an i-butyl group, an s-butyl group, a t-butyl group, a cyclobutyl group, a 1-methyl-cyclopropyl group, a 2-methyl-cyclopropyl group, an n-pentyl group, a 1-methyl-n-butyl group, a 2-methyl-n-butyl group, a 3-methyl-n-butyl group, a 1,1-dimethyl-n-propyl group, a 1,2-dimethyl-n-propyl group, a 2,2-dimethyl-n-propyl group, a 1-ethyl-n-propyl group, a cyclopentyl group, a 1-methyl-cyclobutyl group, a 2-methyl-cyclobutyl group, a 3-methyl-cyclobutyl group, a 1,2-dimethyl-cyclopropyl group, 2,3-dimethyl-cyclopropyl group, a 1-ethyl-cyclopropyl group, a 2-ethyl-cyclopropyl group, an n-hexyl group, a 1-methyl-n-pentyl group, a 2-methyl-n-pentyl group, a 3-methyl-n-pentyl group, a 4-methyl-n-pentyl group, a 1,1-dimethyl-n-butyl group, a 1,2-dimethyl-n-butyl group, a 1,3-dimethyl-n-butyl group, a 2,2-dimethyl-n-butyl group, a 2,3-dimethyl-n-butyl group, a 3,3-dimethyl-n-butyl group, a 1-ethyl-n-butyl group, a 2-ethyl-n-butyl group, a 1,1,2-trimethyl-n-propyl group, a 1,2,2-trimethyl-n-propyl group, a 1-ethyl-1-methyl-n-propyl group, a 1-ethyl-2-methyl-n-propyl group, a cyclohexyl group, a 1-methyl-cyclopentyl group, a 2-methyl-cyclopentyl group, a 3-methyl-cyclopentyl group, a 1-ethyl-cyclobutyl group, a 2-ethyl-cyclobutyl group, a 3-ethyl-cyclobutyl group, a 1,2-dimethyl-cyclobutyl group, a 1,3-dimethyl-cyclobutyl group, a 2,2-dimethyl-cyclobutyl group, a 2,3-dimethyl-cyclobutyl group, a 2,4-dimethyl-cyclobutyl group, a 3,3-dimethyl-cyclobutyl group, a 1-n-propyl-cyclopropyl group, a 2-n-propyl-cyclopropyl group, a 1-i-propyl-cyclopropyl group, a 2-i-propyl-cyclopropyl group, a 1,2,2-trimethyl-cyclopropyl group, a 1,2,3-trimethyl-cyclopropyl group, a 2,2,3-trimethyl-cyclopropyl group, a 1-ethyl-2-methyl-cyclopropyl group, a 2-ethyl-1-methyl-cyclopropyl group, a 2-ethyl-2-methyl-cyclopropyl group, and a 2-ethyl-3-methyl-cyclopropyl group.

The following can be shown as examples of compounds of Formula (1).
Formula (1-1)
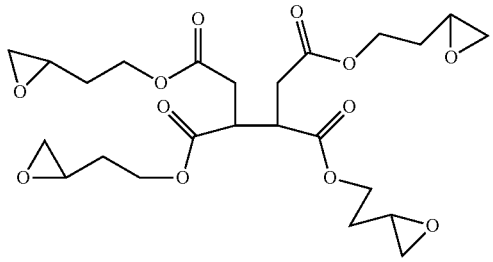
Formula (1-2)
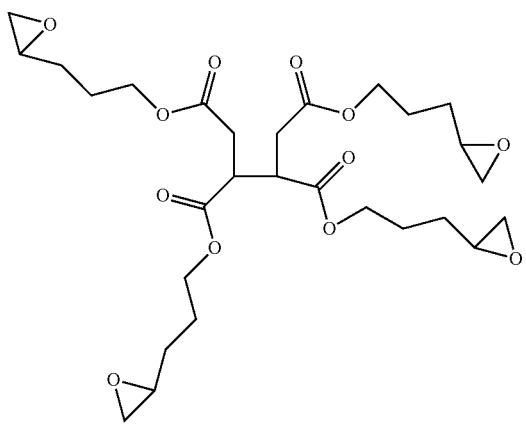
Formula (1-3)
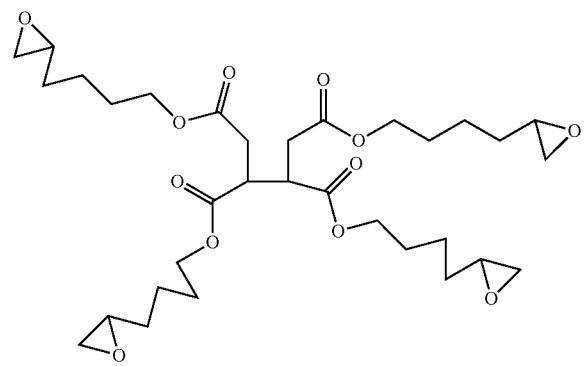
Formula (1-4)
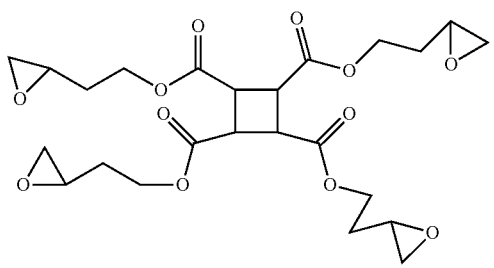
Formula (1-5)
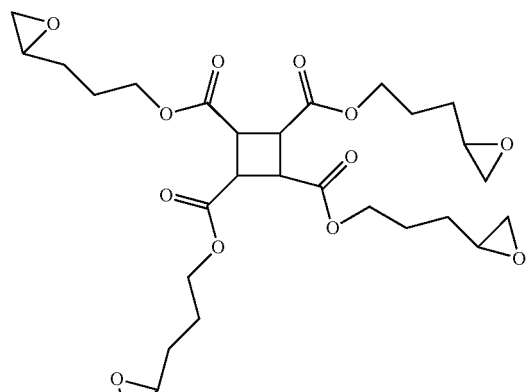
Formula (1-6)
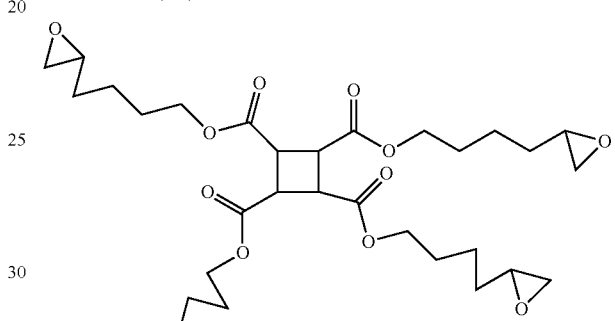
Formula (1-7)
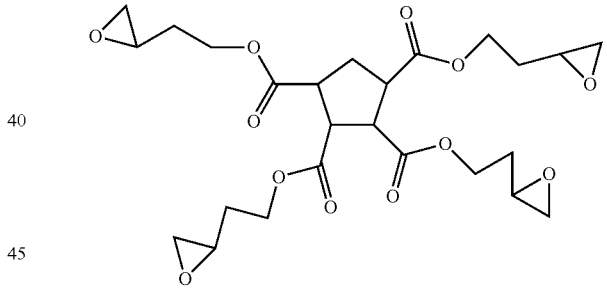
Formula (1-8)
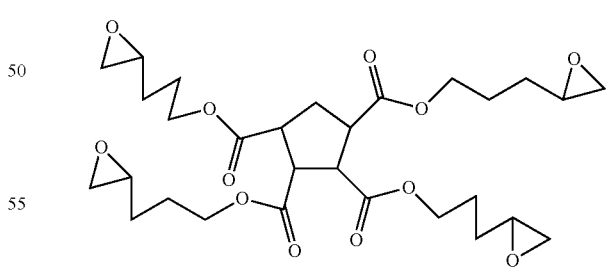
Formula (1-9)
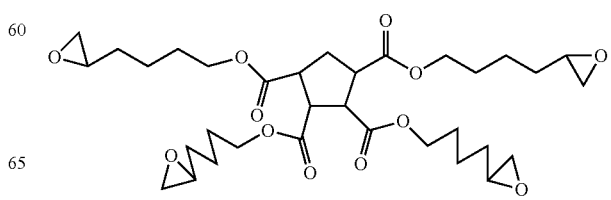

-continued
Formula (1-10)
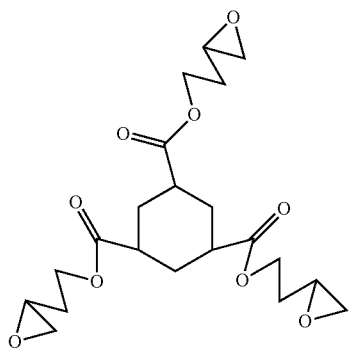
Formula (1-11)
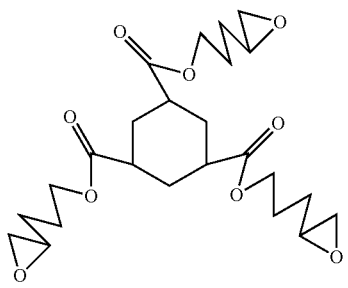
Formula (1-12)
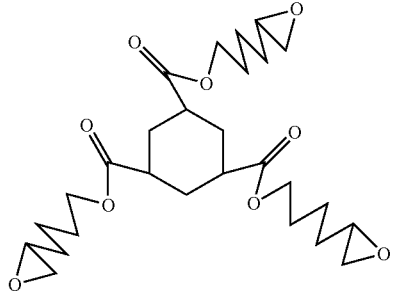
Formula (1-13)
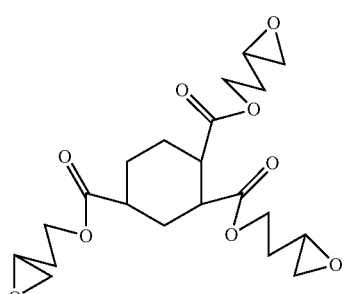
Formula (1-14)
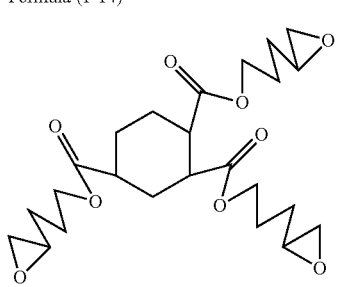
Formula (1-15)
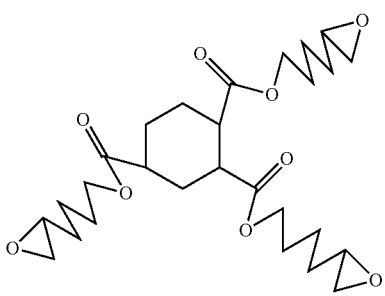
Formula (1-16)
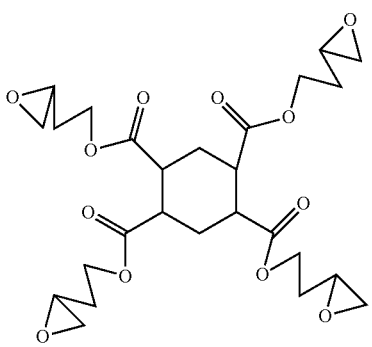
Formula (1-17)
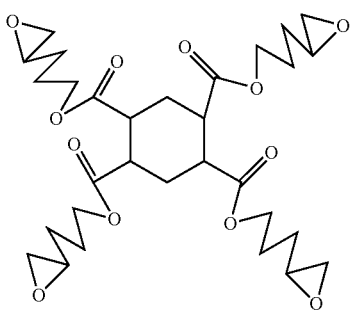
Formula (1-18)
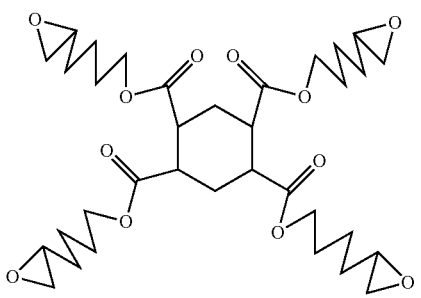

Formula (1-19)
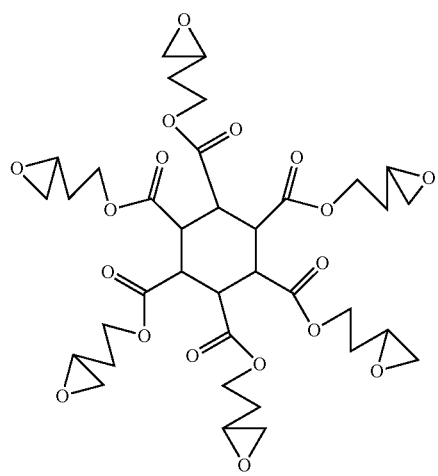
Formula (1-20)
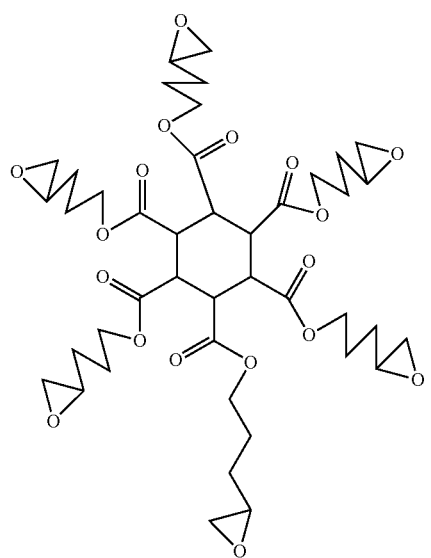
Formula (1-21)
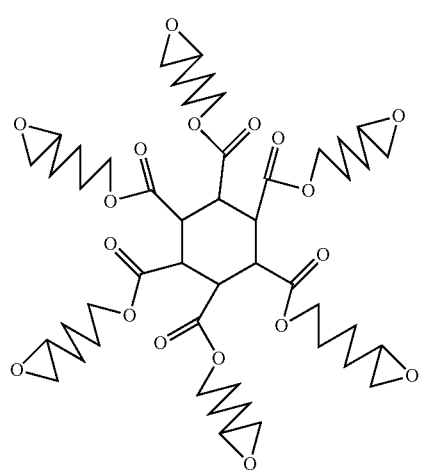
Formula (1-22)
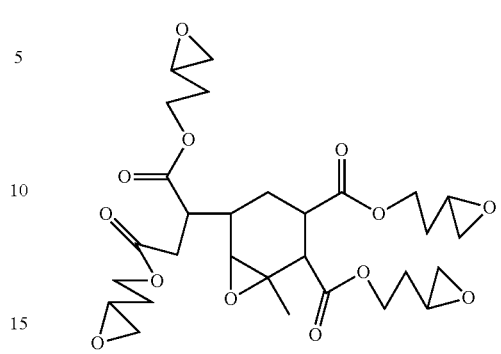
Formula (1-23)
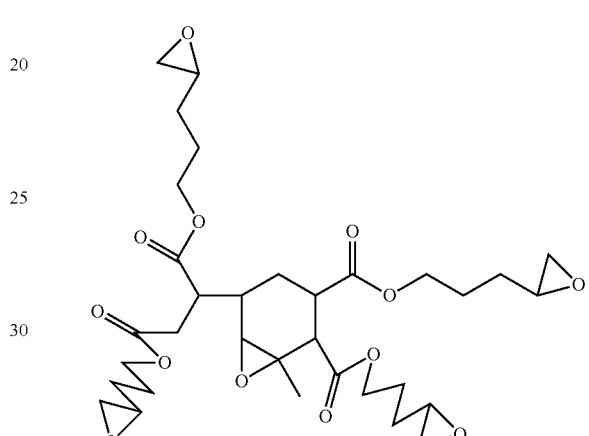
Formula (1-24)
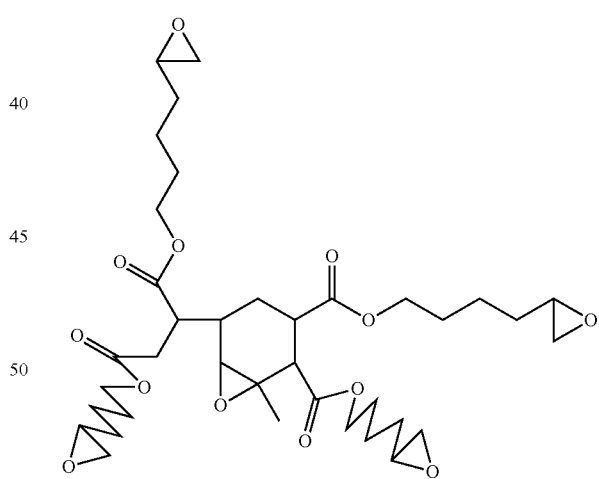
Formula (1-25)
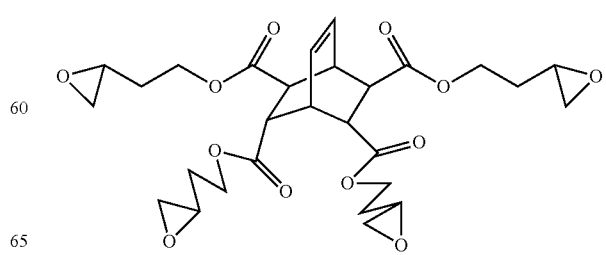

Formula (1-26)

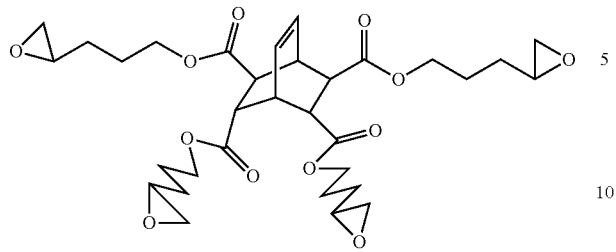

Formula (1-27)

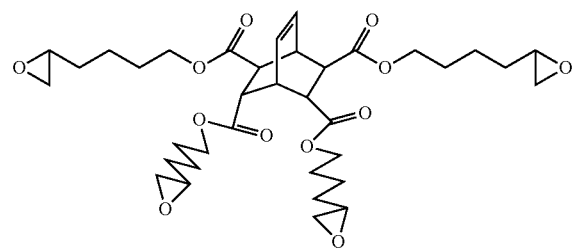

The compound of Formula (1) can be produced by causing, for example, a carboxylic acid of Formula (1') or an anhydride thereof to react with a $C_{4-8}$alkenol and then causing the obtained compound (intermediate) having an unsaturated bond to react with a peroxide. The intermediate can be produced by any method that does not use the reaction of an acid or an acid anhydride with an alkenol. The compound of Formula (1) can be produced by causing the intermediate having an unsaturated bond to react with a peroxide.

Formula (1')

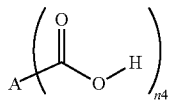

[In Formula (1'), A and n4 have the same definition as described in Formula (1).]

Examples of the carboxylic acid and the acid anhydride thereof include 1,2,3,4-butanetetracarboxylic acid dianhydride, 1,2,3,4-cyclobutanetetracarboxylic acid dianhydride, 1,2,3,4-cyclopentanetetracarboxylic acid dianhydride, 1,3,5-cyclohexanetricarboxylic acid, 1,2,4-cyclohexanetricarboxylic acid, 1,2,4,5-cyclohexanetetracarboxylic acid, 1,2,3,4,5,6-cyclohexanehexacarboxylic acid, bicyclo[2.2.2]7-octene-2,3,5,6-tetracarboxylic acid dianhydride, and 5-(2,5-dioxotetrahydrofuryl)-3-methyl-3-cyclohexene-1,2-dicarboxylic acid anhydride. As the alkenol, for example, 3-buten-1-ol, 4-penten-1-ol, 5-hexen-1-ol, 3-hexen-1-ol, and 3-methyl-3-buten-1-ol can be used. These alkenols are, for example, illustrated below.

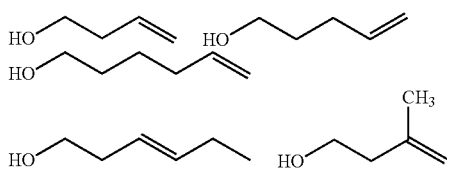

The following can be shown as examples of compounds (intermediates) having an unsaturated bond.

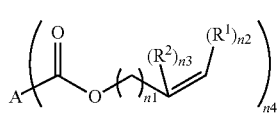

[In the above formula, A is an (n4)-valent $C_{4-20}$ linear hydrocarbon group optionally containing an epoxy group, an (n4)-valent $C_{4-20}$ cyclic hydrocarbon group optionally containing an epoxy group, or an (n4)-valent group of a combination of them; $R^1$ and $R^2$ are each independently a hydrogen atom or a $C_{1-10}$ alkyl group: n1 is an integer of 2 to 6; n2 is an integer of 2; n3 is an integer of 1; and n4 is an integer of 3 to 8.]

More specifically, the epoxy compound of Formula (1) used in the present invention can be obtained by the following method in the case of Formula (1-2) shown above.

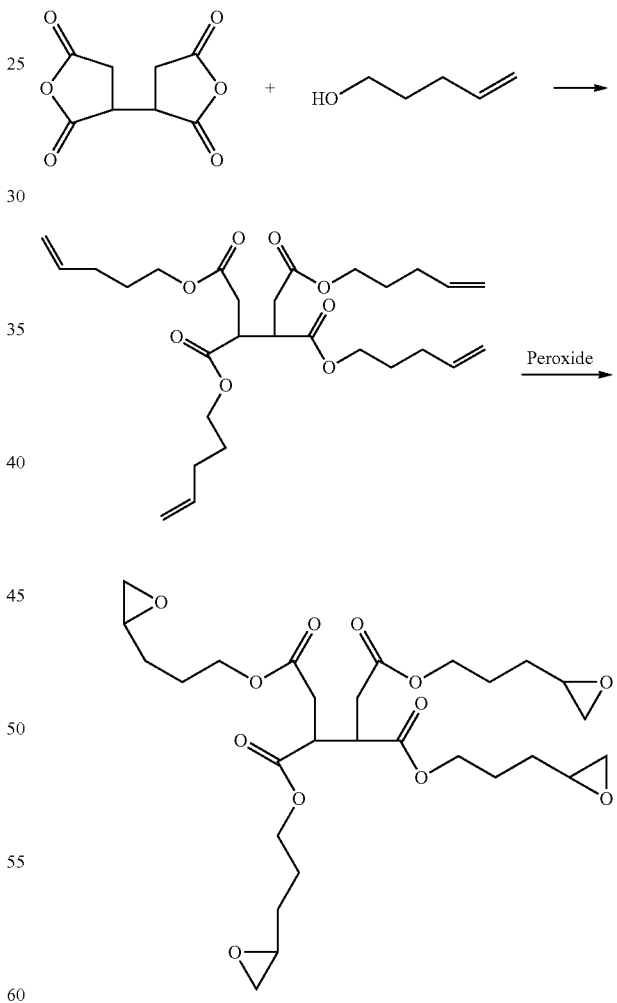

In this reaction, 1,2,3,4-butanetetracarboxylic acid dianhydride reacts with 4-penten-1-ol, thereby synthesizing tetra (4-pentenyl)-1,2,3,4-butanetetracarboxylic acid ester. The reaction is carried out in a solvent such as toluene using a catalyst such as p-toluenesulfonic acid at a temperature from room temperature (for example, 20° C.) to 110° C. for 0 hours to 20 hours. The unsaturated compound can be oxidized with the peroxide to obtain the epoxy compound. As the peroxide, for example, m-chloroperbenzoic acid, peracetic acid, hydrogen peroxide-tungstic acid can be used. The reaction can be carried out in a solvent such as chloroform at 0° C. to 60° C. for 1 hour to 200 hours. Tetra(4-pentenyl)-1,2,3,4-butanetetracarboxylic acid ester that is the intermediate also can be obtained by causing 1,2,3,4-butanetetracarboxylic acid to react with 4-penten-1-ol using a catalyst such as p-toluenesulfonic acid.

The present invention is a curable composition including the epoxy compound of Formula (1) and a curing agent.

Furthermore, the present invention is a curable composition including the epoxy compound of Formula (1) and an acid generator.

The curable composition can further contain a solvent, another epoxy compound, a curing agent, a surfactant, and an adhesion promoter if needed.

A ratio of the solid content in the curable composition of the present invention can be set to 1% by mass to 100% by mass, 5% by mass to 100% by mass, 50% by mass to 100% by mass, or 80% by mass to 100% by mass.

The solid content means a remaining component obtained by removing the solvent from the total components of the curable composition. In the present invention, a liquid epoxy compound is used, and basically, a solvent does not need to be used in order to mix the curing agent or the acid generator with the liquid epoxy compound. However, a solvent can be added if needed. For example, when an acid generator is a solid, the curable composition can be produced by dissolving the acid generator in a solvent such as propylene carbonate and mixing the dissolved acid generator with the liquid epoxy compound. When the acid generator is dissolved in the liquid epoxy compound, a general solvent can be added in order to control viscosity of the obtained curable composition.

Based on the content of the solid content of the curable composition, a content of the epoxy compound of Formula (1) in the curable composition of the present invention is 8% by mass to 99.9% by mass, preferably 40% by mass to 99% by mass, and further preferably 70% by mass to 99% by mass.

Based on the content of the solid content of the curable composition of the present invention, a content of the acid generator can be set to 0.1% by mass to 20% by mass, or 0.1% by mass to 10% by mass.

In the curable composition of the present invention, the acid generator can be contained in a ratio of 0.1% by mass to 20% by mass, or 0.1% by mass to 10% by mass per mass of the epoxy compound of Formula (1).

In the present invention, the epoxy compound of Formula (1) can be used in combination with an epoxy compound other than the epoxy compound of Formula (1). The epoxy compound of Formula (1) and the epoxy compound other than the epoxy compound of Formula (1) can be used in a range of a molar ratio of epoxy groups of 1:0.1 to 1:0.5.

The following can be shown as examples of the epoxy compound other than the epoxy compound of Formula (1).

A solid epoxy compound, tris-(2,3-epoxypropyl)-isocyanurate (Formula (2-1), trade name: TEPIC, manufactured by Nissan Chemical Industries, Ltd.).

Formula (2-1)

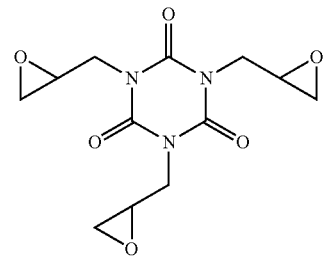

A liquid epoxy compound, trade name: EPIKOTE 828 (Formula (2-2), manufactured by Japan Epoxy Resin Co. Ltd.).

Formula (2-2)

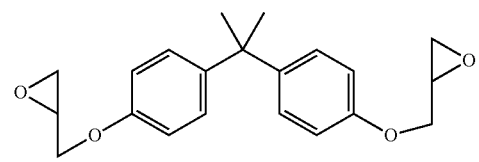

A liquid epoxy compound, trade name: YX8000 (Formula (2-3), manufactured by Japan Epoxy Resin Co. Ltd.).

Formula (2-3)

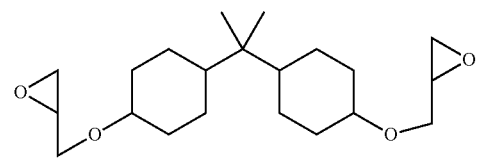

A liquid epoxy compound, trade name: DME100, (Formula (2-4), manufactured by New Japan Chemical Co., Ltd.).

Formula (2-4)

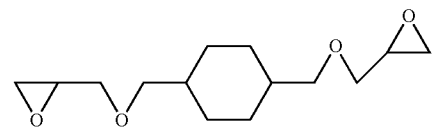

A liquid epoxy compound, trade name: CE-2021P (Formula (2-5), manufactured by Daicel Corporation).

Formula (2-5)

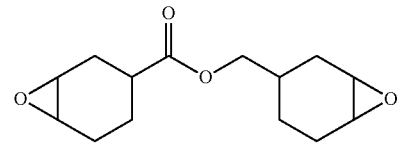

In the present invention, as liquid epoxy compounds, the following tris-(3,4-epoxybutyl)-isocyanurate (Formula (2-6)), tris-(4,5-epoxypentyl)-isocyanurate (Formula (2-7)), and tris-(5,6-epoxyhexyl)-isocyanurate (Formula (2-8)) can be used.

Formula (2-6)

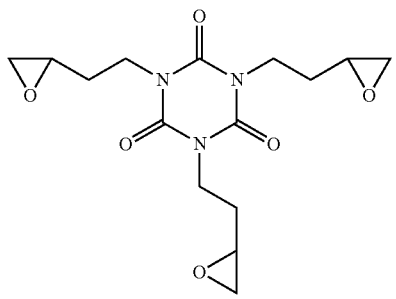

Formula (2-7)

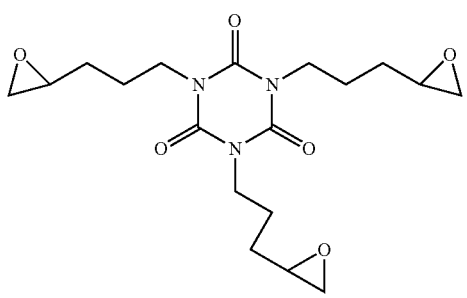

Formula (2-8)

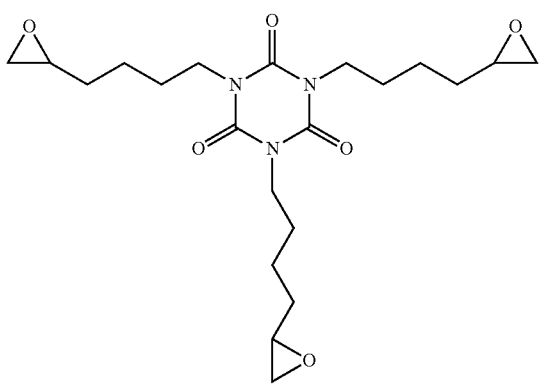

Formula (2-9)

(2-9-1)

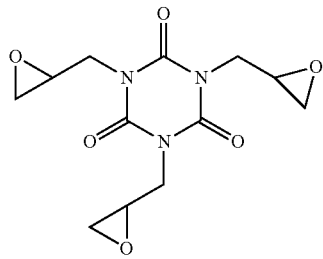

(2-9-2)

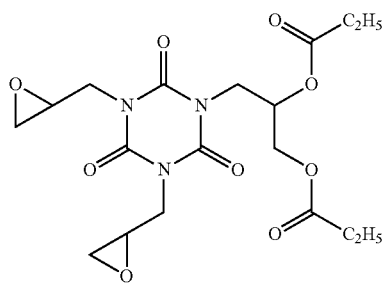

(2-9-3)

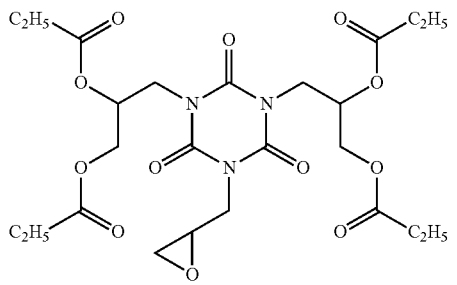

(2-9-4)

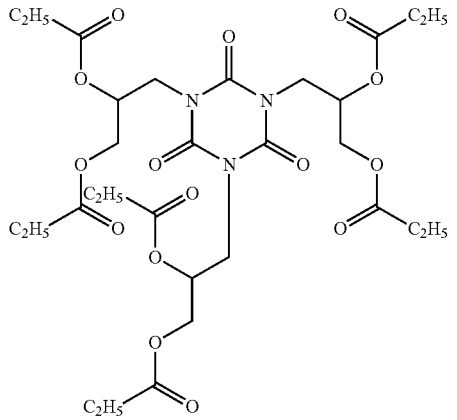

A modified liquid epoxy compound made by adding 0.8 mol of propionic anhydride to 1 mol of tris-(2,3-epoxypropyl)-isocyanurate (Formula (2-9), manufactured by Nissan Chemical Industries, Ltd., trade name: TEPIC-PAS B22). In Formula (2-9), each compound of Formula (2-9-1), Formula (2-9-2), Formula (2-9-3), and Formula (2-9-4) is contained in a molar ratio of about 35%:45%:17%:3%.

A modified liquid epoxy compound made bay adding 0.4 mol of propionic anhydride to 1 mol of tris-(2,3-epoxypropyl)-isocyanurate (Formula (2-10), manufactured by Nissan Chemical Industries, Ltd., trade name: TEPIC-PAS B26). In Formula (2-10), each compound of Formula (2-10-1), Formula (2-10-2), and Formula (2-10-3) is contained in a molar ratio of about 60%:32%:8%.

Formula (2-10)

(2-10-1)
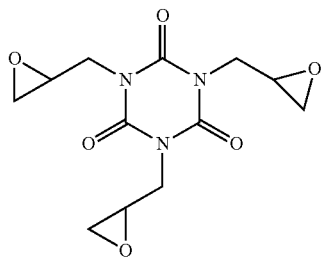

(2-10-2)
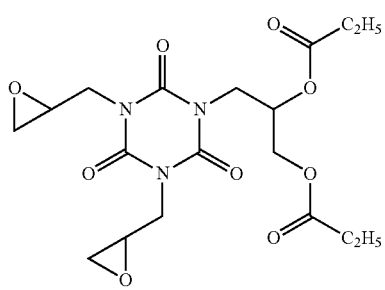

(2-10-3)
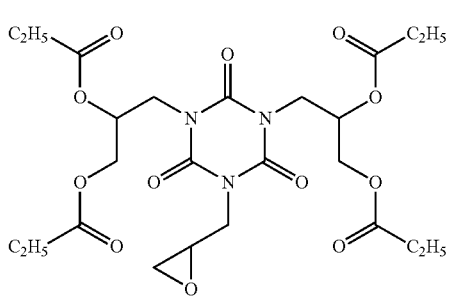

In addition to the epoxy compounds, compounds such as vinyl ether compounds, oxetane compounds, carbonate compounds, and dithiocarbonate compounds can be used as a cationic curable monomer in the present invention.

The vinyl group-containing compounds (such as vinyl ether compounds) are not particularly limited as long as the compounds are vinyl group-containing compounds. Examples of the vinyl group-containing compounds include 2-hydroxyethyl vinyl ether (HEVE), diethylene glycol monovinyl ether (DEGV), 2-hydroxybutyl vinyl ether (HBVE), and triethylene glycol divinyl ether. Vinyl compounds having a substituent such as an alkyl group and an allyl group at an α position and/or a β position also can be used. Vinyl ether compounds including a cyclic ether group such as an epoxy group and/or an oxetane group can be used. Examples of the vinyl ether compounds include oxynorbornene divinyl ether and 3,3-dimethanoloxetane divinyl ether. Hybrid compounds having a vinyl group and a (meth)acrylic group can be used. Examples of the hybrid compounds include 2-(2-vinyloxyethoxy)ethyl(meth)acrylate (VEEA, VEEM). These compounds can be used singly or in combination of two or more of them.

The oxetanyl group-containing compounds (oxetane compounds) are not particularly limited as long as the compounds contain the oxetanyl group. Examples of the oxetanyl group-containing compounds include 3-ethyl-3-(phenoxymethyl)oxetane (POX), di[1-ethyl(3-oxetanyl)]methyl ether (DOX), 3-ethyl-3-(2-ethylhexyloxymethyl)oxetane (EHOX), 3-ethyl-3-{[3-(triethoxysilyl)propoxy]methyl}oxetane (TESOX), oxetanyl silsesquioxane (OX-SQ), and phenol novolac oxetane (PNOX-1009). A hybrid compound having an oxetanyl group and a (meth)acrylic group (1-ethyl-3-oxetanylmethyl(meth)acrylate) can be used. These oxetane-based compounds can be used singly or in combination of two or more of them.

As the carbonate compounds and the dithiocarbonate compounds are not particularly limited as long as the compounds contain a carbonate group or a dithiocarbonate group in their molecules.

In the present invention, the curable composition including the epoxy compound of Formula (1) and a curing agent can be obtained.

As the curing agent, at least one selected from the group consisting of an acid anhydride, amines, a phenol resin, a polyamide resin, imidazoles, and a polymercaptan can be used. Among them, the acid anhydride and the amines are particularly preferable. When these curing agents are solids, the curing agents can be used by dissolving in a solvent. However, evaporation of the solvent causes decrease in strength and water resistance due to decrease in density of the cured product and generation of fine pores, and thus, curing agents themselves being a liquid state at a normal temperature and under a normal pressure is preferable.

The epoxy compound can contain the curing agent in a ratio of 0.5 equivalents to 1.5 equivalents, and preferably 0.8 equivalents to 1.2 equivalents per equivalent of the epoxy group is the epoxy compound. The equivalent of the curing agent to the epoxy compound can be shown by an equivalent ratio of curable groups in the curing agent to the epoxy groups.

Examples of the phenol resin include phenol novolac resins and cresol novolac resins.

Examples of the amines include piperidine, N,N-dimethylpiperadine, triethylenediamine, 2,4,6-tris(dimethylaminomethyl)phenol, benzyldimethylamine, 2-(dimethylaminomethyl)phenol, diethylenetriamine, triethylenetetramine, tetraethylenepentamine, diethylaminopropylamine, N-aminoethylpiperazine, di(1-methyl-2-aminocyclohexyl)methane, menthene-diamine, isophorone-diamine, diaminodicyclohexylmethane, 1,3-diaminomethylcyclohexane, xylenediamine, m-phenylenediamine, diaminodiphenylmethane, and diaminodiphenylsulfone. Among these amines, diethylenetriamine, triethylenetetramine, tetraethylenepentamine, diethylaminopropylamine, N-aminoethylpiperazine, di(1-methyl-2-aminocyclohexyl)methane, menthene-diamine, isophorone-diamine, and diaminodicyclohexylmethane being liquid can be preferably used.

The polyamide resin is a polyamide-amine having primary amines and secondary amines in its molecule prepared by condensation of dimer acids and polyamines.

Examples of the imidazoles include 2-methylimidazole, 2-ethyl-4-methylimidazole, 1-cyanoethyl-2-undecylimidazolium trimellitate, and epoxy-imidazole adducts.

The polymercaptan is, for example, a polymercaptan in which a mercaptan group exists at the terminal of a polypropylene glycol chain, and a polymercaptan in which a mercaptan group exists at the terminal of a polyethylene glycol chain. A liquid polymercaptan is preferable.

As the acid anhydride, an acid anhydride of a compound in which a plurality of carboxy groups exist in one molecule is preferable. Examples of the acid anhydride include phthalic anhydride, trimellitic anhydride, pyromellitic dianhydride, benzophenone-tetracarboxylic dianhydride, ethyleneglycol bistrimellitate, glycerol tristrimellitate, maleic anhydride, tetrahydrophthalic anhydride, methyltetrahydrophthalic anhydride, endomethylene tetrahydrophthalic anhydride, methyl endomethylene tetrahydrophthalic anhydride, methylbutenyltetrahydrophthalic anhydride, dodecenylsuccinic anhydride, hexahydrophthalic anhydride, methylhexahydrophthalic anhydride, succinic anhydride, methylcyclohexane dicarboxylic anhydride, and chlorendic anhydride.

Among these acid anhydrides, methyltetrahydrophthalic anhydride, methyl-5-norbornene-2,3-dicarboxylic anhydride(methyl nadic anhydride, methyl himic anhydride), hydrogenated methyl nadic anhydride, methylbutenyltetrahydrophthalic anhydride, dodecenylsuccinic anhydride, methylhexahydrophthalic anhydride, and a mixture of methylhexahydrophthalic anhydride and hexahydrophthalic anhydride that are liquid at normal temperature and under normal pressure are preferable. These liquid acid anhydrides have a viscosity of 10 mPas to 1000 mPas measured at 25° C. In the acid anhydride group, one acid anhydride group is calculated as one equivalent.

When the cured product is obtained from the curable composition of the present invention, the curing aid may be adequately used at the same time. Examples of the curing aid include organic phosphorus compounds such as triphenylphosphine and tributylsphine; quaternary phosphonium salts such as ethyltriphenylphosphonium bromide and diethyl tetrabutylphosphonium dithiophosphate; 1,8-diazabicyclo[5,4,0]undecane-7-ene, a salt of 1,8-diazabicyclo[5,4,0]undecane-7-ene and octylic acid, zinc octylate, and quaternary ammonium salts such as tetrabutylammonium bromide. These curing aids can be contained in a ratio of 0.001 parts by mass to 0.1 parts by mass per part by mass of the curing agent.

In the present invention, the curable composition can be obtained by mixing the epoxy compound of Formula (1) and the curing agent and optionally the curing aid. The mixing of these compounds can be carried out by using a reaction flask or a stirring impeller.

The mixing is carried out by a heat mixing method at a temperature of 10° C. to 100° C. for 0.5 hours to 1 hour.

The obtained curable composition has an appropriate viscosity for using as a liquid sealant. The curable composition of the present invention can be prepared to have any viscosity. In order to use the curable composition for a transparent sealant for an LED or the like by a casting method, a potting method, a dispenser method, and a printing method, the curable composition can partially seal the LED or the like at any positions. The epoxy resin cured product is obtained by directly implementing the curable composition in a liquid state to an LED or the like by the method described above, and thereafter, drying and curing.

The cured product obtained from the curable composition of the present invention can be obtained by applying the curable composition to a substrate or pouring the curable composition into a casting plate coated with a release agent, pre-curing at a temperature of 100° C. to 120° C., and curing at a temperature of 120° C. to 200° C.

A heating time for the curing is about 1 hour to 12 hours, and preferably about 2 hours to 5 hours.

A thickness of a coating film obtained from the curable composition of the present invention can be selected in a range of about 0.01 μm to 10 mm depending on applications of the cured product.

The curable composition can contain a solvent if needed. Examples of the solvent include alcohols such as methanol and ethanol; ethers such as tetrahydrofuran; glycol ethers such as ethylene glycol monomethyl ether and ethylene glycol monoethyl ether; ethylene glycol alkyl ether acetates such as methyl cellosolve acetate and ethyl cellosolve acetate; diethylene glycols such as diethylene glycol monomethyl ether, diethylene glycol monoethyl ether, diethylene glycol dimethyl ether, diethylene glycol diethyl ether, and diethylene glycol ethylmethyl ether; propylene glycol monoalkyl ethers such as propylene glycol methyl ether, propylene glycol ethyl ether, propylene glycol propyl ether, and propylene glycol butyl ether; propylene glycol monoalkyl ether acetates such as propylene glycol methyl ether acetate, propylene glycol ethyl ether acetate, propylene glycol propyl ether acetate, and propylene glycol butyl ether acetate; propylene glycol alkyl ether acetates such as propylene glycol methyl ether propionate, propylene glycol ethyl ether propionate, propylene glycol propyl ether propionate, and propylene glycol butyl ether propionate; aromatic hydrocarbons such as toluene and xylene; ketones such as methyl ethyl ketone, cyclohexanone, 4-hydroxy-4-methyl-2-pentanone; esters such as methyl acetate, ethyl acetate, propyl acetate, butyl acetate, ethyl 2-hydroxypropionate, methyl 2-hydroxy-2-methylpropionate, ethyl 2-hydroxy-2-methylpropionate, methyl hydroxyacetate, ethyl hydroxyacetate, butyl hydroxyacetate, methyl lactate, ethyl lactate, propyl lactate, butyl lactate, methyl 3-hydroxypropionate, ethyl 3-hydroxypropionate, propyl 3-hydroxypropionate, butyl 3-hydroxypropionate, methyl 2-hydroxy-3-methylbutyrate, methyl methoxyacetate, ethyl methoxyacetate, propyl methoxyacetate, butyl methoxyacetate, methyl ethoxyacetate, ethyl ethoxyacetate, propyl ethoxyacetate, butyl ethoxyacetate, methyl propoxyacetate, ethyl propoxyacetate, propyl propoxyacetate, butyl propoxyacetate, methyl butoxyacetate, ethyl butoxyacetate, propyl butoxyacetate, butyl butoxyacetate, methyl 2-methoxypropionate, ethyl 2-methoxypropionate, propyl 2-methoxypropionate, butyl 2-methoxypropionate, methyl 2-ethoxypropionate, ethyl 2-ethoxypropionate, propyl 2-ethoxypropionate, butyl 2-ethoxypropionate, methyl 2-butoxypropionate, ethyl 2-butoxypropionate, propyl 2-butoxypropionate, butyl 2-butoxypropionate, methyl 3-methoxypropionate, ethyl 3-methoxypropionate, propyl 3-methoxypropionate, butyl 3-methoxypropionate, methyl 3-ethoxypropionate, ethyl 3-ethoxypropionate, propyl 3-ethoxypropionate, butyl 3-ethoxypropionate, methyl 3-propoxypropionate, ethyl 3-ethoxypropionate, butyl 3-ethoxypropionate, methyl 3-propoxypropionate, ethyl 3-propoxypropionate, propyl 3-propoxypropionate, butyl 3-propoxypropionate, methyl 3-butoxypropionate, ethyl 3-butoxypropionate, propyl 3-butoxypropionate, and butyl 3-butoxypropionate.

In the present invention, the curable composition including the epoxy compound of Formula (1) and the acid generator can be obtained. As the acid generator, the photo acid generator or the thermal acid generator can be used.

The photo acid generator and the thermal acid generator are not particularly limited as long as the generators directly or indirectly generate acid by light irradiation or heating.

Specific examples of the photo acid generator may include a triazine-based compound, an acetophenone derivative compound, a disulphone-based compound, a diazomethane-based compound, a sulfonic acid derivative compound, onium salts such as an iodonium salt, a sulfonium salt, a phosphonium salt, a selenium salt, a metallocene complex, and an iron-arene complex.

In the onium salts used as the photo acid generator, examples of the iodonium salt include diphenyliodonium chloride, diphenyliodonium trifluoromethanesulfonate, diphenyliodonium mesylate, diphenyliodonium tosylate, diphenyliodonium bromide, diphenyliodonium tetrafluoroborate, diphenyliodonium hexafluoroantimonate, diphenyliodonium hexafluoroarsenate, bis(p-tert-butylphenyl)iodonium hexafluorophosphate, bis(p-tert-butylphenyl)iodonium mesylate, bis(p-tert-butylphenyl)iodonium tosylate, bis(p-tert-butylphenyl)iodonium methanesulfonate, bis(p-tert-butylphenyl)iodonium tetrafluoroborate, bis(p-tert-butylphenyl)iodonium chloride, bis(p-chlorophenyl)iodonium chloride, and bis(p-chlorophenyl)iodonium tetrafluoroborate. Examples of the iodonium salt further include bis(alkylphenyl)iodonium salts such as bis(4-tert-butylphenyl)iodonium hexafluorophosphate; alkoxycarbonylalkoxy-trialkylaryl iodonium salts (such as 4-[1-ethoxycarbonyl-ethoxy)phenyl]-(2,4,6-trimethylphenyl)-iodonium hexafluorophosphate); bis(alkoxyaryl)iodonium salts (such as (4-methoxyphenyl)phenyliodonium hexafluoroantimonate).

Examples of the sulfonium salt include triphenylsulfonium salts such as triphenylsulfonium chloride, triphenylsulfonium bromide, tri(p-methoxyphenyl)sulfonium tetrafluoroborate, tri(p-methoxyphenyl)sulfonium hexafluorophosphonate, tri(p-ethoxyphenyl)sulfonium tetrafluoroborate, triphenylsulfonium triflate, triphenylsulfonium hexafluoroantimonate, triphenylsulfonium hexafluorophosphate; and sulfonium salts such as (4-phenylthiophenyl)diphenylsulfonium hexafluoroantimonate, (4-phenylthiophenyl)diphenylsulfonium hexafluorophosphate, bis[4-(diphenylsulfonio)phenyl]sulfide-bis-hexafluoroantimonate, bis[4-(diphenylsulfonio)phenyl]sulfide-bis-hexafluorophosphate, and (4-methoxyphenyl)diphenylsulfonium hexafluoroantimonate).

Examples of the phosphonium salt include phosphonium salts such as triphenylphosphonium chloride, triphenylphosphonium bromide, tri(p-methoxyphenyl)phosphonium tetrafluoroborate, tri(p-methoxyphenyl)phosphonium hexafluorophosphonate, tri(p-ethoxyphenyl)phosphonium tetrafluoroborate, 4-chloro-benzenediazonium hexafluorophosphate, and benzyltriphenylphosphonium hexafluoroantimonate The selenium salts such as triphenylselenium hexafluorophosphate and the metallocene complexes such as (η5 or η6-isopropylbenzene) (η5-cyclopentadienyl) iron (II) hexafluorophosphate can be included.

Following compounds can be used as the photo acid generator.

Formula (B-1)

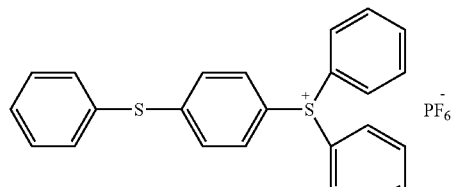

Formula (B-2)

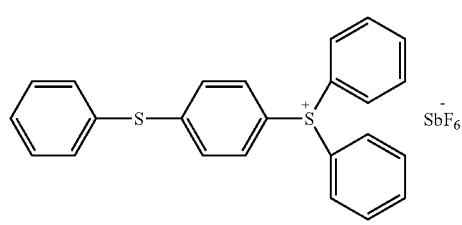

Formula (B-3)

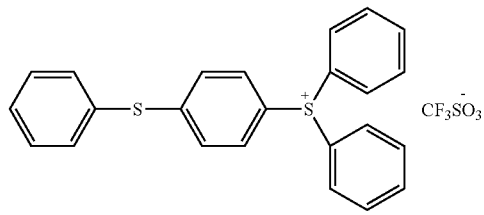

Formula (B-4)

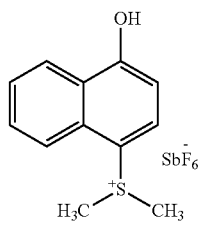

Formula (B-5)

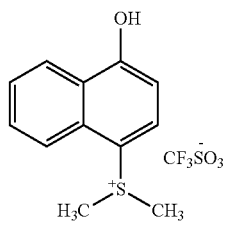

Formula (B-6)

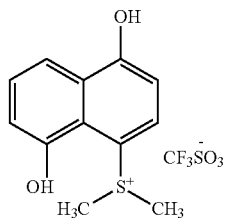

Formula (B-7)

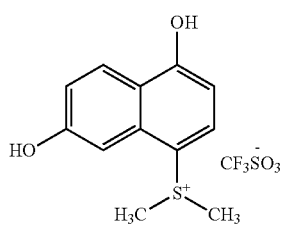

Formula (B-8)

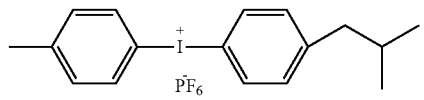

Formula (B-9)

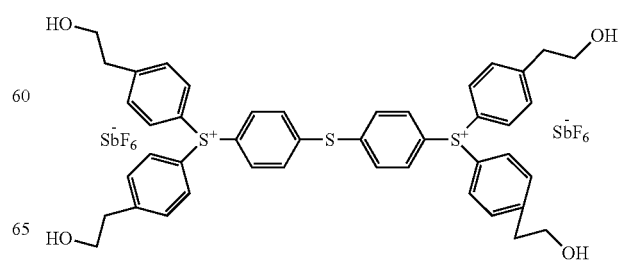

-continued
Formula (B-10)
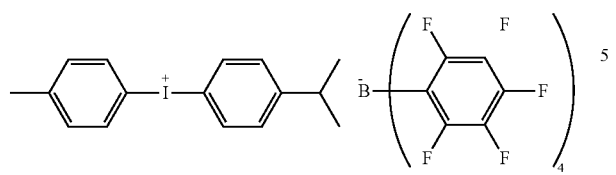
Formula (B-11)
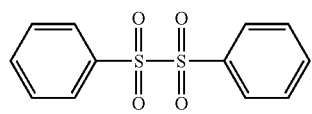
Formula (B-12)
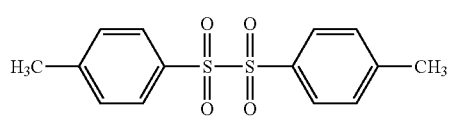
Formula (B-13)
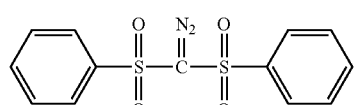
Formula (B-14)
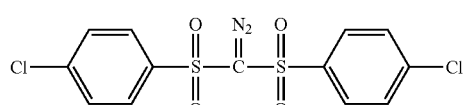
Formula (B-15)
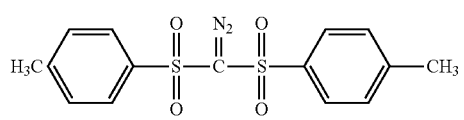
Formula (B-16)
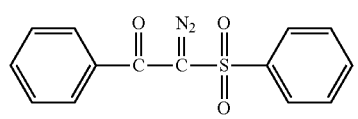
Formula (B-17)
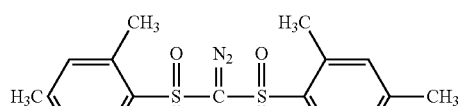
Formula (B-18)
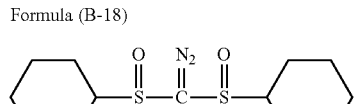
Formula (B-19)
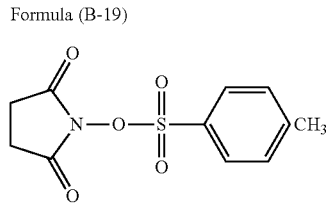
-continued
Formula (B-20)
Formula (B-21)
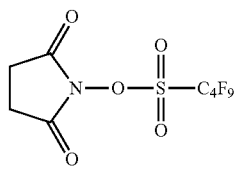
Formula (B-22)
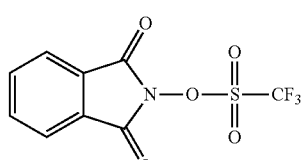
Formula (B-23)
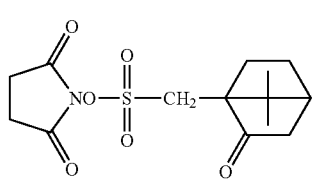
Formula (B-24)
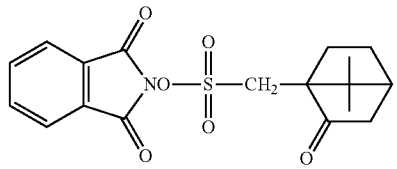
Formula (B-25)
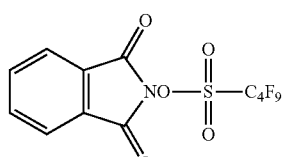
Formula (B-26)
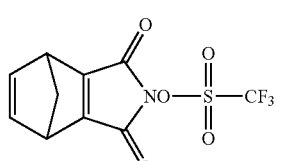
Formula (B-27)
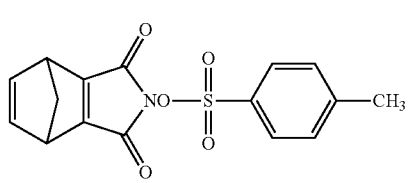

Formula (B-28)
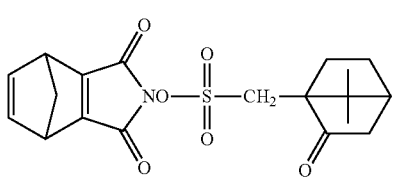
Formula (B-29)
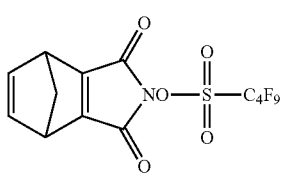
Formula (B-30)
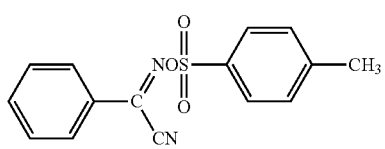
Formula (B-31)
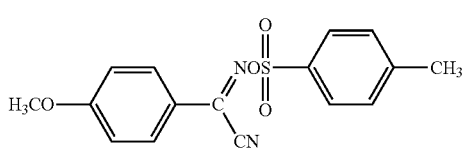
Formula (B-32)
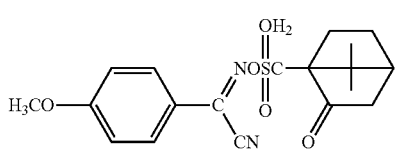
Formula (B-33)
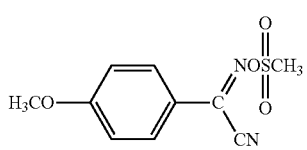
Formula (B-34)
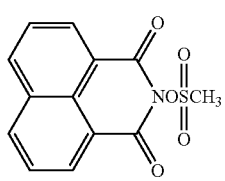
Formula (B-35)
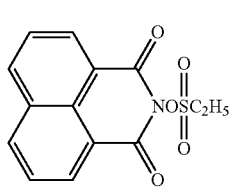
Formula (B-36)
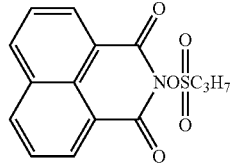
Formula (B-37)
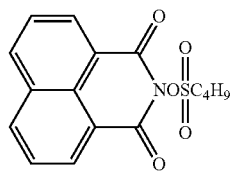
Formula (B-38)
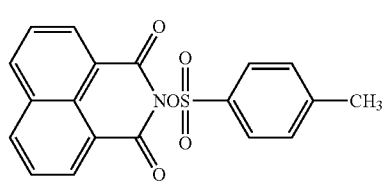
Formula (B-39)
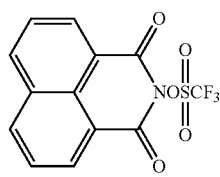
Formula (B-40)
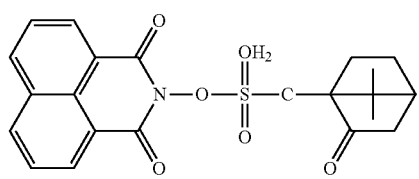
Formula (B-41)
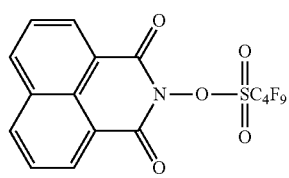
Formula (B-42)
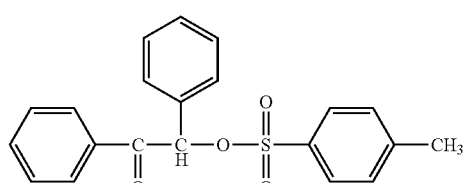
Formula (B-43)
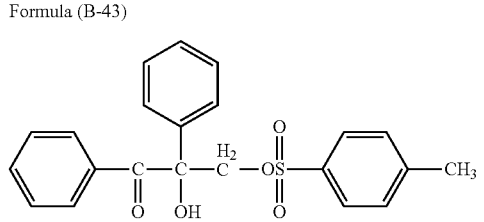

Formula (B-44)
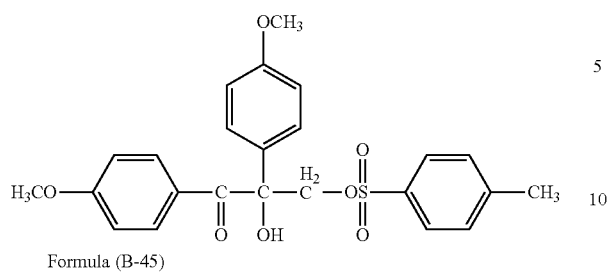
Formula (B-45)
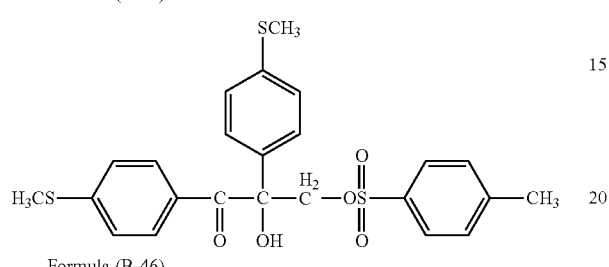
Formula (B-46)
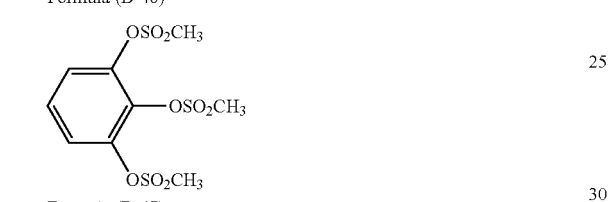
Formula (B-47)
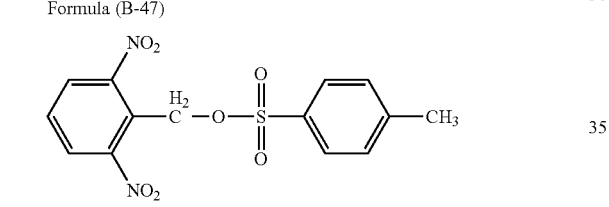
Formula (B-48)
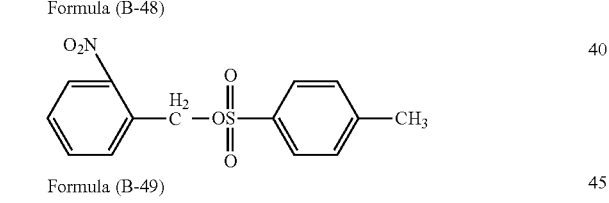
Formula (B-49)
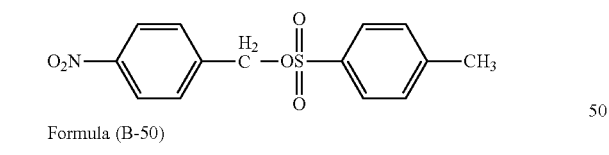
Formula (B-50)
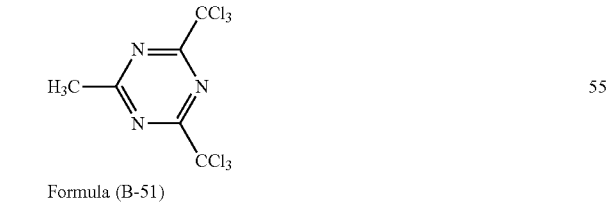
Formula (B-51)
Formula (B-52)
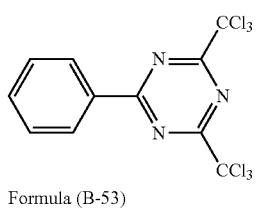
Formula (B-53)
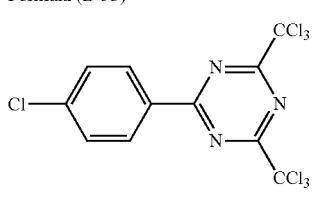
Formula (B-54)
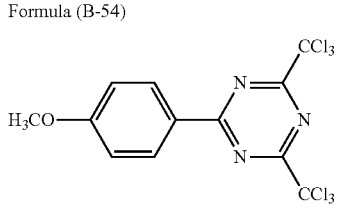
Formula (B-55)
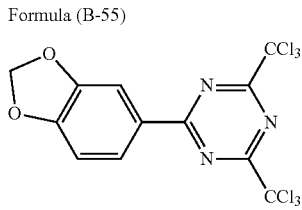
Formula (B-56)
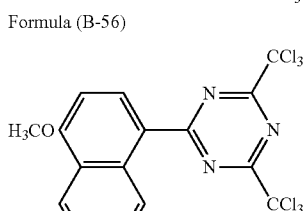
Formula (B-57)
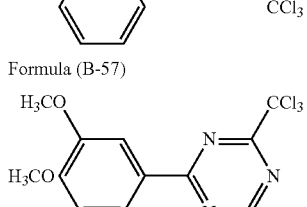
Formula (B-58)
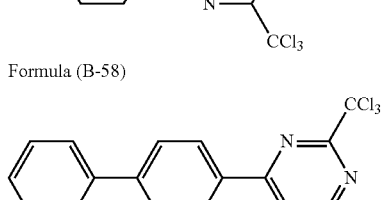
Formula (B-59)
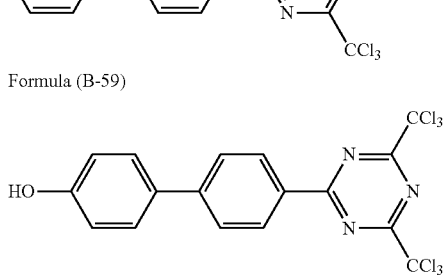

Formula (B-60)
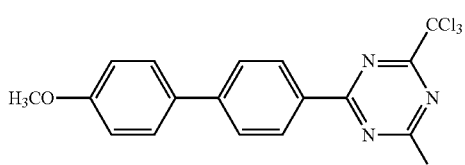

Formula (B-61)
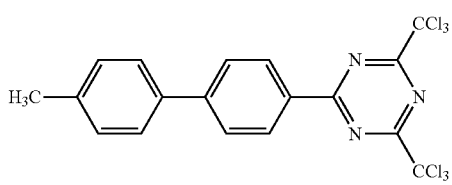

Formula (B-62)
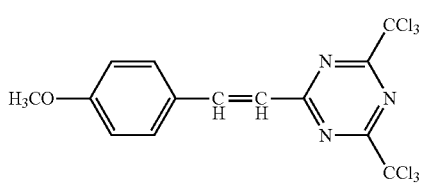

Formula (B-63)
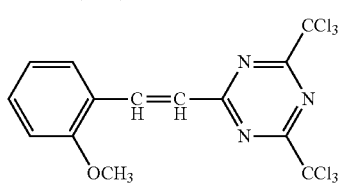

Formula (B-64)
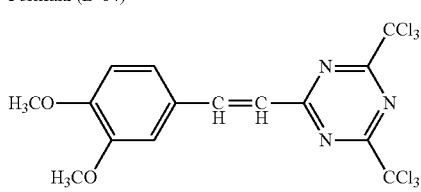

Formula (B-65)
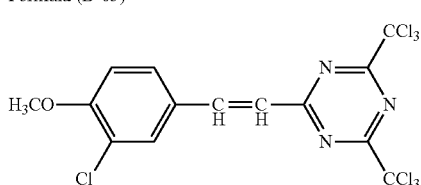

Formula (B-66)
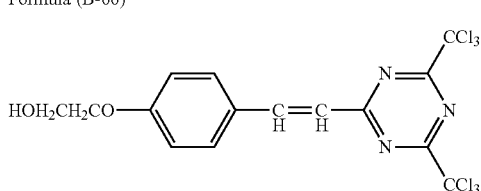

Formula (B-67)
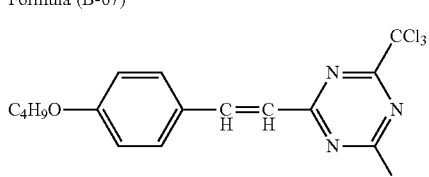

The sulfonium salt compound or the iodonium salt compound is preferable as the photo acid generator. Examples of anion species thereof include $CF_3SO_3^-$, $C_4F_9SO_3^-$, $C_8F_{17}SO_3^-$, camphorsulfonic acid anions, tosic acid anions, $BF_4^-$, $PF_6^-$, $AsF_6^-$, and $SbF_6^-$. Particularly, the anion species of phosphorus hexafluoride and antimony hexafluoride that show strong acidity are preferable.

As the photo acid generator, for example, the compounds of Formula (B-1), Formula (B-2), Formula (B-3), Formula (B-8), Formula (B-9), and Formula (B-10) are preferable and the compounds of Formula (B-1) and Formula (B-2) are particularly preferable. These photo acid generators can be used singly or in combination of two or more of them.

As the thermal acid generator, for example, a sulfonium salt and a phosphonium salt are included, and the sulfonium salt is preferably used.

As examples of the thermal acid generator, the following compounds can be shown.

Formula (C-1)
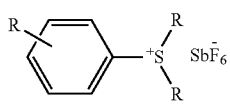

Formula (C-2)
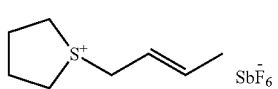

[in Formula (C-1), each R is independently a $C_{1-12}$ alkyl group and a $C_{6-20}$ aryl group, and particularly the $C_{1-12}$ alkyl group is preferable.]

These thermal acid generators can be used singly or in combination of two or more of them.

The curable composition can include a solvent. The solvents described above can be used for the solvent.

The composition can contain additives in common use if needed. Example of these additives include a pigment, a colorant, a thickening agent, a sensitizer, a defoaming agent, a leveling agent, a coatability improving agent, a lubricant agent, a stabilizer (an antioxidant, a heat stabilizer, a light stabilizer, and the like), a plasticizer, a surfactant, a solution promoter, a filler, an antistatic agent, and a curing agent. These additives can be used singly or in combination of two or more of them.

In order to improve coatability, the surfactant can be added to the curable composition of the present invention. Examples of the surfactant include a fluorinated surfactant, a silicone-based surfactant, and a nonionic surfactant. However, the surfactant is not particularly limited to these surfactants. The surfactants can be used singly or in combination of two or more of them.

Among these surfactants, the fluorinated surfactant is preferable because of its high improvement effect of coatability. Specific examples of the fluorinated surfactants include trade name: EFTOP [registered trademark] EF301, EF303, and EF 352 (manufactured by Mitsubishi Materials Electronic Chemicals Co., Ltd. (Tohkem products Corporation)); trade name: MEGAFAC [registered trademark] F171, F173, R-30, R-08, R-90, BL-20, and F-482 (manufactured by DIC Corporation); trade name: FLUORAD FC430 and FC431 (manufactured by Sumitomo 3M Limited); trade name: AashiGuard [registered trademark] AG710, Surflon [registered trademark]S-382, SC101, SC102, SC103, SC104, SC105, and SC106 (manufactured by Asahi Glass Co., Ltd.). However, the fluorinated surfactants are not limited to these surfactants.

Based on the solid content of the curable composition, an amount of added surfactant in the curable composition of the present invention is 0.0008% by mass to 4.5% by mass, preferably 0.0008% by mass to 2.7% by mass, and more preferably 0.0008% by mass to 1.8% by mass.

Adhesion promoters can be added to the curable resin composition of the present invention for the purpose of improving adhesion to the substrate after development. Examples of these adhesion promoters include chlorosilanes such as trimethylchlorosilane, dimethylvinylchlorosilane, methyldiphenylchlorosilane, and chloromethyldimethylchlorosilane; alkoxy silanes such as trimethylmethoxysilane, dimethyldiethoxysilane, methyldimethoxysilane, dimethylvinylethoxysilane, diphenyldimethoxysilane, and phenyltriethoxysilane; silazanes such as hexamethyldisilazane, N,N'-bis(trimethylsilyl)urea, dimethyltrimethylsilylamine, and trimethylsilylimidazole; silanes such as vinyltrichlorosilane, γ-chloropropyltrimethoxysilane, γ-aminopropyltriethoxysilane, γ-methacryloxypropyltrimethoxysilane, γ-glycidoxypropyltrimethoxysilane, and γ-(N-piperidinyl)propyltrimethoxysilane; heterocyclic compounds such as benzotriazole, benzimidazole, indazole, imidazole, 2-mercaptobenzimidazole, 2-mercaptobenzothiazole, 2-mercaptobenzoxazole, urazole, thiouracil, mercaptoimidazole, and mercaptopyrimidine; ureas such as 1,1-dimethyl urea and 1,3-dimethyl urea, and thiourea compounds. The adhesion promoters can be used singly or in combination of two or more of them.

Based on the solid content of the curable composition, an amount of added adhesion promoter in the curable composition of the present invention is usually 18% by mass or less, preferably 0.0008% by mass to 9% by mass, and more preferably 0.04% by mass to 9% by mass.

The curable composition of the present invention may contain the sensitizer. Examples of usable sensitizer include anthracene, phenothiazine, perylene, thioxanthone, and benzophenonethioxanthone. As sensitizing dyes, a thiopyrylium salt-based dye, a merocyanine-based dye, a quinolone-based dye, a styrylquinoline-based dye, a ketocoumarin-based dye, a thioxanthene-based dye, a xanthene-based dye, an oxonol-based dye, a cyanine-based dye, a rhodamine-based dye, and a pyrylium salt-based dye can be cited. The anthracene-based sensitizer is particularly preferable. The sensitivity is dramatically improved by using the anthracene-based sensitizer with a cationic curing catalyst (a radiation sensitive cationic polymerization initiator) and the anthracene-based sensitizer has a function of radical polymerization initiation. Consequently, in a hybrid curing system as in the present invention, in which the cationic curing system and the radical curing system are used at the same time, catalyst species can be simplified. As specific anthracene compounds, compounds such as dibutoxyanthracene and dipropoxyanthraquinone are effective.

Based on the solid content of the curable composition, an amount of added sensitizer in the curable composition of the present invention is 0.01% by mass to 20% by mass, and preferably 0.01% by mass to 10% by mass.

In the present invention, the curable composition containing the epoxy compound of Formula (1) and the photo acid generator can be applied onto a substrate and cured by light irradiation. Also, the curable composition can be heated before or after the light irradiation.

In the present invention, the curable composition containing the epoxy compound of Formula (1) and the thermal acid generator can be applied onto a substrate and cured by heating.

In the present invention, the curable composition containing the epoxy compound of Formula (1) and the thermal acid generator and the photo acid generator can be applied onto a substrate and cured by light irradiation after heating.

Examples of a method for applying the curable composition of the present invention onto a substrate may include a flow coating method, a spin coating method, a spray coating method, a screen printing method, a casting method, a bar coating method, a curtain coating method, a roll coating method, a gravure coating method, a dipping method, and a slit method.

Depending on applications of the cured product, a thickness of a coating film formed from the curable composition of the present invention can be selected from a range of about 0.01 μm to 10 mm. For example, when the curable composition is used for a photoresist, the thickness can be set to about 0.05 μm to 10 μm (particularly, about 0.1 μm to 5 μm); when the curable composition is used for a printed circuit board, the thickness can be set to about 10 μm to 5 mm (particularly, about 100 μm to 1 mm); and when the curable composition is used for an optical thin film, the thickness can be set to about 0.1 μm to 100 μm (particularly, about 0.3 μm to 50 μm).

Examples of the irradiation light or exposure light when the photo acid generator is used include gamma ray, X ray, ultraviolet ray, and visible light ray. Usually, the visible light ray and the ultraviolet ray, and particularly the ultraviolet ray may be frequently used.

A wavelength of the light is, for example, about 150 nm to 800 nm, preferably about 150 nm to 600 nm, further preferably about 200 nm to 400 nm, and particularly about 300 nm to 400 nm.

An amount of radiated light depends on the thickness of the coating film, and, for example, about 2 mJ/cm$^2$ to 20000 mJ/cm$^2$, and preferably about 5 mJ/cm$^2$ to 5000 mJ/cm$^2$.

A light source can be selected depending on the type of exposure light. For example, in the case of the ultraviolet ray, a low pressure mercury lamp, a high pressure mercury lamp, a super high pressure mercury lamp, a deuterium lamp, a halogen lamp, laser light (such as helium-cadmium laser and excimer laser) can be used. By this light irradiation, a curing reaction of the curable composition of the present invention containing the epoxy compound of Formula (1) and the photo acid generator proceeds.

Heating when the thermal acid generator is used or heating of the coating film after the light irradiation if necessary when the photo acid generator is used is carried out, for example, at about 60° C. to 250° C., and preferably about 100° C. to 200° C. Heating time can be selected from a range of about 3 seconds or more (for example, about 3 seconds to 5 hours), for example, about 5 seconds to 2 hours, preferably about 20 seconds to 30 minutes, and usually about 1 minute to 3 hours (for example, about 5 minutes to 2.5 hours).

Further, the coating film formed on the substrate may be subjected to pattern exposure to form a pattern or an image (for example, to produce a printed circuit board or the like). This pattern exposure may be carried out by laser light scanning or maybe carried out by light irradiation through a photomask. The pattern or the image can be formed by developing (or dissolving) a non-irradiation region (an unexposed region) generated by this pattern exposure with a developing solution.

As the developing solution, an alkaline aqueous solution and an organic solvent can be used.

Examples of the alkaline aqueous solution may include aqueous solutions of alkali metal hydroxides such as potassium hydroxide, sodium hydroxide, potassium carbonate, and sodium carbonate; aqueous solutions of quaternary ammonium hydroxides such as tetramethyl ammonium hydroxide, tetraethyl ammonium hydroxide, and choline; and aqueous solutions of amines such as ethanolamine, propylamine, and ethylenediamine.

The alkaline aqueous solution is generally an aqueous solution having a concentration of 10% by mass or less, and an aqueous solution having a concentration of 0.1% by mass to 3.0% by mass is used. The alkaline aqueous solution also can be used by adding alcohols and surfactants. The added amounts of the alcohols and surfactants are each preferably 0.05 parts by mass to 10 parts by mass relative to 100 parts by mass of the alkaline aqueous solution. Among the alkaline aqueous solutions, the aqueous solution of tetramethyl ammonium hydroxide of 0.1% by mass to 2.38% by mass can be used.

As the organic solvent serving as the developing liquid, general organic solvent can be used. Examples of the organic solvent include acetone, acetonitrile, toluene, dimethylformamide, methanol, ethanol, isopropanol, propylene glycol methyl ether, propylene glycol ethyl ether, propylene glycol propyl ether, propylene glycol butyl ether, propylene glycol methyl ether acetate, propylene glycol ethyl ether acetate, propylene glycol propyl ether acetate propylene glycol butyl ether acetate, ethyl lactate, and cyclohexanone. These organic solvents can be used singly or in combination of two or more of them. Particularly, propylene glycol methyl ether, propylene glycol methyl ether acetate, ethyl lactate, and the like can be preferably used.

EXAMPLES

The following devices were used for each measurement.
NMR: FT-NMR (ECX300), manufactured by JEOL Ltd.
LC-MS: Liquid chromatograph mass spectrometer (Alliance-ZQ-LC-MS), manufactured by Waters Corporation
GC-MS: Gas chromatograph mass spectrometer (GC-MC QP5050A), manufactured by Shimadzu Corporation
Viscosity measurement: E-type viscometer (VISCNIC ED), manufactured by Tokimec Inc.
Transmittance measurement: Ultraviolet-visible-near infrared spectrophotometer (UV-3600), manufactured by Shimadzu Corporation
Bending test: Autograph (AGS-X series), manufactured by Shimadzu Corporation Linear expansion coefficient and glass-transition temperature measurement:
Thermo-mechanical analyzer (TMA Q400), manufactured by TA Instruments
The following epoxy compounds were prepared.
[Preparation of Epoxy Compounds]

Synthesis Example 1

Synthesis of tetra(5,6-epoxyhexyl)-1,2,3,4-butanetetracarboxylic acid ester

To a reactor equipped with a Dean-Stark apparatus and a condenser, 10 g of 1,2,3,4-butanetetracarboxylic acid dianhydride, 1 g of p-toluenesulfonic acid monohydrate, 100 mL of toluene, and 22 g of 5-hexen-1-ol were charged, and the mixture was caused to react at a reflux temperature for 3 hours. After completion of the reaction, the mixture was washed with sodium bicarbonate water and washed with water, and then concentrated. The concentrated mixture was purified by silica gel chromatography (as a developing solvent, hexane:ethyl acetate was used in a volume ratio of hexane:ethyl acetate=95:5→80:20) to obtain 23 g of tetra (5-hexenyl)-1,2,3,4-butanetetracarboxylic acid ester as a light yellow liquid.

H-NMR (300 MHz, CDCl$_3$): δ=5.86-5.72 (m, 4H), 5.04-4.95 (m, 8H), 4.11-4.06 (m, 8H), 3.32-3.29 (m, 2H), 2.83-2.74 (m, 2H), 2.43-2.36 (m, 2H), 2.11-2.04 (m, 8H), 1.68-1.59 (m, 8H), 1.51-1.39 (m, 8H),

GC-MS (CI): m/z=563 (M+H).

To a reactor, 23 g of tetra(5-hexenyl)-1,2,3,4-butanetetracarboxylic acid ester and 300 ml of chloroform were charged, and the mixture was cooled to 0° C. to 10° C. Thereafter, 44 g of m-chloroperbenzoic acid was added and a temperature of the mixture was raised to room temperature and the mixture was caused to react for 143 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=50:50→10:90) to obtain 25 g of a light yellow liquid.

The obtained compound was tetra(5,6-epoxyhexyl)-1,2, 3,4-butanetetracarboxylic acid ester corresponding to Formula (1-3). The viscosity was 490 mPa·s at 25° C. This epoxy compound was determined as (i-1).

H-NMR (300 MHz, CDCl$_3$): δ=4.15-4.07 (m, 8H), 3.34-3.27 (m, 2H), 2.91-2.88 (m, 4H), 2.83-2.73 (m, 6H), 2.48-2.37 (m, 6H), 1.74-1.48 (m, 24H),

LC-MS (ESI): m/z=649.6 (M+Na).

Synthesis Example 2

Synthesis of tetra(4,5-epoxypentyl)-1,2,3,4-butanetetracarboxylic acid ester

To a reactor equipped with a Dean-Stark apparatus and a condenser, 14 g of 1,2,3,4-butanetetracarboxylic acid dianhydride, 1 g of p-toluenesulfonic acid monohydrate, 100 mL of toluene, and 26 g of 4-penten-1-ol were charged, and the mixture was caused to react at a reflux temperature for 6 hours. After completion of the reaction, the mixture was washed with sodium bicarbonate water and washed with water, and then concentrated. The concentrated mixture was purified by silica gel chromatography (as a developing solvent, hexane:ethyl acetate was used in a volume ratio of hexane:ethyl acetate of 80:20) to obtain 31 g of tetra(4-pentenyl)-1,2,3,4-butanetetracarboxylic acid ester as a colorless liquid.

H-NMR (300 MHz, CDCl$_3$): δ=5.86-5.72 (m, 4H), 5.07-4.98 (m, 8H), 4.13-4.07 (m, 8H), 3.34-3.30 (m, 2H), 2.84-2.75 (m, 2H), 2.44-2.37 (m, 2H), 2.15-2.08 (m, 8H), 1.77-1.68 (m, 8H),

GC-MS (CI): m/z=507 (M+H),

To a reactor 30 g of tetra(4-pentenyl)-1,2,3,4-butanetetracarboxylic acid ester and 300 ml of chloroform were charged, and the mixture was cooled to 0° C. to 10° C. Thereafter, 65 g of m-chloroperbenzoic acid was added and a temperature of the mixture was raised to room temperature and the mixture was caused to react for 22 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=30:70→10:90) to obtain 33 g of a colorless liquid.

The obtained compound was tetra(4,5-epoxypentyl)-1,2,3,4-butanetetracarboxylic acid ester corresponding to Formula (1-2). The viscosity was 734 mPa·s at 25° C. This epoxy compound was determined as (i-2).

H-NMR (300 MHz, CDCl$_3$): δ=4.15-4.11 (m, 8H), 3.29 (m, 2H), 2.96-2.90 (m, 4H), 2.83-2.75 (m, 6H), 2.50-2.37 (m, 6H), 1.84-1.50 (m, 16H),

LC-MS (ESI): m/z=593.4 (M+Na).

Synthesis Example 3

Synthesis of tetra(3,4-epoxybutyl)-1,2,3,4-butanetetracarboxylic acid ester

To a reactor equipped with a Dean-Stark apparatus and a condenser, 10 g of 1,2,3,4-butanetetracarboxylic acid dianhydride, 1 g of p-toluenesulfonic acid monohydrate, 100 mL of toluene, and 17 g of 3-buten-1-ol were charged, and the mixture was caused to react at a reflux temperature for 6 hours. After completion of the reaction, the mixture was washed with sodium bicarbonate water and washed with water, and then concentrated. The concentrated mixture was purified by silica gel chromatography (as a developing solvent, hexane:ethyl acetate was used in a volume ratio of hexane:ethyl acetate of 80:20) to obtain 21 g of tetra(3-butenyl)-1,2,3,4-butanetetracarboxylic acid ester as a colorless liquid.

H-NMR (300 MHz, CDCl$_3$): δ=5.84-5.70 (m, 4H), 5.14-5.06 (m, 8H), 4.17-4.11 (m, 8H), 3.32-3.28 (m, 2H), 2.84-2.78 (m, 2H), 2.43-2.35 (m, 10H),

LC-MS (ESI):m/z=451.3 (M+H).

To a reactor, 21 g of tetra(3-butenyl)-1,2,3,4-butanetetracarboxylic acid ester and 500 ml of chloroform were charged, and the mixture was cooled to 0° C. to 10° C. Thereafter, 51 g of m-chloroperbenzoic acid was added and a temperature of the mixture was raised to room temperature and the mixture was caused to react for 28 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate of 30:70) to obtain 20 g of a light yellow liquid. Subsequently, 200 g of toluene and 4 g of activated carbon were added, and the mixture was stirred for 2 hours. The activated carbon was filtered and the solvent of the filtrate was evaporated to obtain 20 g of a colorless liquid.

The obtained compound was tetra(3,4-epoxybutyl)-1,2,3,4-butanetetracarboxylic acid ester corresponding to Formula (1-1). The viscosity was 1196 mPa·s at 25° C. This epoxy compound was determined as (i-3).

H-NMR (300 MHz, CDCl$_3$): δ=4.29-4.23 (m, 8H), 3.38-3.34 (m, 2H), 3.04-2.96 (m, 4H), 2.88-2.77 (m, 6H), 2.53-2.42 (m, 6H), 2.01-1.90 (m, 4H), 1.83-1.73 (m, 4H),

LC-MS (ESI): m/z=515.3 (M+H).

Synthesis Example 4

Synthesis of tetra(4,5-epoxypentyl)-1,2,3,4-cyclobutanetetracarboxylic acid ester To a reactor equipped with a Dean-Stark apparatus and a condenser, 10 g of 1,2,3,4-cyclobutanetetracarboxylic acid dianhydride, 1 g of p-toluenesulfonic acid monohydrate, 100 mL of toluene, and 21 g of 5-hexen-1-ol were charged, and the mixture was caused to react at a reflux temperature for 4 hours. After completion of the reaction, the mixture was washed with sodium bicarbonate water and washed with water, and then concentrated to obtain 25 g of tetra(4-pentenyl)-1,2,3,4-cyclobutanetetracarboxylic acid ester as a light yellow liquid.

H-NMR (300 MHz, CDCl$_3$): δ=5.86-5.72 (m, 4H), 5.07-4.98 (m, 8H), 4.18-4.04 (m, 8H), 3.75 (s, 4H), 2.17-2.08 (m, 8H), 1.77-1.68 (m, 8H),

LC-MS (ESI): m/z=505.5 (M+H).

To a reactor, 25 g of tetra(4-pentenyl)-1,2,3,4-cyclobutanetetracarboxylic acid ester and 500 ml of chloroform were charged, and the mixture was cooled to 0° C. to 10° C. Thereafter, 55 g of m-chloroperbenzoic acid was added and a temperature of the mixture was raised to room temperature and the mixture was caused to react for 24 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=30:70→0:100) to obtain 28 g of a light yellow liquid.

The obtained compound was tetra(4,5-epoxypentyl)-1,2,3,4-cyclobutanetetracarboxylic acid ester corresponding to Formula (1-5). The viscosity was 426 mPa·s at 25° C. This epoxy compound was determined as (i-4).

H-NMR (300 MHz, CDCl$_3$): δ=4.23-4.08 (m, 8H), 3.74 (s, 4H), 2.97-2.91 (m, 4H), 2.78-2.75 (m, 4H), 2.51-2.45 (m, 4H), 1.88-1.47 (m, 16H),

LC-MS (ESI): m/z=591.3 (M+Na).

Synthesis Example 5

Synthesis of tetra(4,5-epoxypentyl)-1,2,3,4-cyclopentanetetracarboxylic acid ester To a reactor equipped with a Dean-Stark apparatus and a condenser, 12 g of 1,2,3,4-cyclopentanetetracarboxylic acid dianhydride, 0.5 g of p-toluenesulfonic acid monohydrate, 100 mL of toluene, and 21 g of 4-penten-1-ol were charged, and the mixture was caused to react at a reflux temperature for 2.5 hours. After completion of the reaction, the mixture was washed with sodium bicarbonate water and washed with water, and then concentrated. The concentrated mixture was purified by silica gel chromatography (as a developing solvent, hexane:ethyl acetate was used in a volume ratio of hexane:ethyl acetate of 90:10) to obtain 24 g of tetra(4-pentenyl)-1,2,3,4-cyclopentanetetracarboxylic acid ester as a colorless liquid.

H-NMR (300 MHz, CDCl$_3$): δ=5.86-5.72 (m, 4H), 5.06-4.96 (m, 8H), 4.14-4.02 (m, 8H), 3.42-3.39 (m, 2H), 3.07-3.04 (m, 2H), 2.85-2.77 (m, 1H), 2.41-2.35 (m, 1H), 2.14-2.09 (m, 8H), 1.76-1.66 (m, 8H),

GC-MS (CI): m/z=519 (M+H).

To a reactor, 24 g of tetra(4-pentenyl)-1,2,3,4-cyclopentanetetracarboxylic acid ester and 300 ml of chloroform were charged, and the mixture was cooled to 0° C. to 10° C. Thereafter, 50 g of m-chloroperbenzoic acid was added and a temperature of the mixture was raised to room temperature and the mixture was caused to react for 20 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=20:80→10:90) to obtain 24 g of a light yellow liquid.

The obtained compound was tetra(4,5-epoxypentyl)-1,2,3,4-cyclopentanetetracarboxylic acid ester corresponding to Formula (1-8). The viscosity was 818 mPa·s at 25° C. This epoxy compound was determined as (i-5).

H-NMR (300 MHz, CDCl$_3$): δ=4.16-4.07 (m, 8H), 3.40-3.37 (m, 2H), 3.09-3.06 (m, 2H), 2.93-2.92 (m, 4H), 2.77-2.73 (m, 5H), 2.50-2.47 (m, 5H), 1.84-1.53 (m, 16H),

GC-MS (CI): m/z=583 (M+H).

Synthesis Example 6

Synthesis of tri(5,6-epoxyhexyl)-1,3,5-cyclohexanetricarboxylic acid ester

To a reactor equipped with a Dean-Stark apparatus and a condenser, 13 g of 1,3,5-cyclohexanetricarboxylic acid, 0.6 g of p-toluenesulfonic acid monohydrate, 100 mL of toluene, and 20 g of 5-hexen-1-ol were charged, and the mixture was caused to react at a reflux temperature for 9 hours. After completion of the reaction, the mixture was washed with sodium bicarbonate water and washed with water, and then concentrated to obtain 29 g of tri(5-hexenyl)-1,3,5-cyclohexanetricarboxylic acid ester as a brown liquid.

H-NMR (300 MHz, CDCl$_3$): δ=5.83-5.74 (m, 3H), 5.04-4.95 (m, 6H), 4.11-4.06 (m, 6H), 2.38-1.42 (m, 27H),

GC-MS (CI): m/z=463 (M+H).

To a reactor, 28 g of tri(5-hexenyl)-1,3,5-cyclohexanetricarboxylic acid ester and 500 ml of chloroform were charged, and the mixture was cooled to 0° C. to 10° C. Thereafter, 50 g of m-chloroperbenzoic acid was added and a temperature of the mixture was raised to room temperature and the mixture was caused to react for 20 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=20:80→10:90) to obtain 23 g of a colorless liquid.

The obtained compound was tri(5,6-epoxyhexyl)-1,3,5-cyclohexanetricarboxylic acid ester corresponding to Formula (1-12). The viscosity was 264 mPa·s at 25° C. This epoxy compound was determined as (i-6).

H-NMR (300 MHz, CDCl$_3$): δ=4.12-4.08 (t, 6H), 2.91 (s, 3H), 2.77-2.74 (m, 3H), 2.49-2.46 (m, 3H), 2.38-1.52 (m, 27H),

LC-MS (ESI): m/z=533.4 (M+Na).

Synthesis Example 7

Synthesis of tri(4,5-epoxypentyl)-1,3,5-cyclohexanetricarboxylic acid ester

To a reactor equipped with a Dean-Stark apparatus and a condenser, 12 g of 1,3,5-cyclohexanetricarboxylic acid, 0.5 g of p-toluenesulfonic acid monohydrate, 100 mL of toluene, and 16 g of 4-penten-1-ol were charged, and the mixture was caused to react at a reflux temperature for 5.5 hours. After completion of the reaction, the mixture was washed with sodium bicarbonate water and washed with water, and then concentrated to obtain 24 g of tri(4-pentenyl)-1,3,5-cyclohexanetricarboxylic acid ester as a light yellow liquid.

H-NMR (300 MHz, CDCl$_3$): δ=5.86-5.72 (m, 3H), 5.06-4.97 (m, 6H), 4.12-4.08 (m, 6H), 2.43-1.48 (m, 21H),

GC-MS (CI): m/z=421 (M+H).

To a reactor, 23 g of tri(4-pentenyl)-1,3,5-cyclohexanetricarboxylic acid ester and 500 ml of chloroform were charged, and the mixture was cooled to 0° C. to 10° C. Thereafter, 50 g of m-chloroperbenzoic acid was added and a temperature of the mixture was raised to room temperature and the mixture was caused to react for 24 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=50:50→30:70) to obtain 24 g of a light yellow liquid. Subsequently, 240 g of toluene and 2 g of activated carbon were added, and the mixture was stirred for 3 hours. The activated carbon was filtered and the solvent of the filtrate was evaporated to obtain 23 g of a colorless liquid.

The obtained compound was tri(4,5-epoxypentyl)-1,3,5-cyclohexanetricarboxylic acid ester corresponding to Formula (1-11). The viscosity was 309 mPa·s at 25° C. This epoxy compound was determined as (i-7).

H-NMR (300 MHz, CDCl$_3$): δ=4.16-4.14 (t, 6H), 2.97-2.91 (m, 3H), 2.78-2.75 (m, 3H), 2.50-2.47 (m, 3H), 2.43-1.47 (m, 21H),

GC-MS (CI): m/z=469 (M+H).

Synthesis Example 8

Synthesis of tri(5,6-epoxyhexyl)-1,2,4-cyclohexanetricarboxylic acid ester

To a reactor equipped with a Dean-Stark apparatus and a condenser, 12 g of 1,2,4-cyclohexanetricarboxylic acid, 1 g of p-toluenesulfonic acid monohydrate, 150 mL of toluene, and 20 g of 5-hexen-1-ol were charged, and the mixture was caused to react at a reflux temperature for 11 hours. After completion of the reaction, the mixture was washed with sodium bicarbonate water and washed with water, and then concentrated. The concentrated mixture was purified by silica gel chromatography (as a developing solvent, hexane:ethyl acetate was used in a volume ratio of hexane:ethyl acetate of 90:10) to obtain 25 g of tri(5-hexenyl)-1,2,4-cyclohexanetricarboxylic acid ester as a light yellow liquid.

H-NMR (300 MHz, CDCl₃): δ=5.86-5.72 (m, 3H), 5.04-4.95 (m, 6H), 4.13-4.05 (m, 6H), 3.25 (s, 1H), 2.48-1.26 (m, 26H),

LC-MS (ESI): m/z=485.62 (M+Na).

To a reactor, 24 g of tri(5-hexenyl)-1,2,4-cyclohexanetricarboxylic acid ester and 500 ml of chloroform were charged, and the mixture was cooled to 0° C. to 10° C. Thereafter, 43 g of m-chloroperbenzoic acid was added and a temperature of the mixture was raised to room temperature and the mixture was caused to react for 41 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=50:50→0:100) to obtain 26 g of a light yellow liquid.

The obtained compound was tri(5,6-epoxyhexyl)-1,2,4-cyclohexanetricarboxylic acid ester corresponding to Formula (1-15). The viscosity was 349 mPa·s at 25° C. This epoxy compound was determined as (i-8).

H-NMR (300 MHz, CDCl₃): δ=4.13-4.06 (m, 6H), 3.24 (m, 1H), 2.91 (m, 3H), 2.77-2.74 (m, 3H), 2.49-2.43 (m, 4H), 2.34-2.30 (m, 3H), 2.03-1.85 (m, 2H), 1.69-1.38 (m, 20H),

LC-MS (ESI): m/z=533.3 (M+Na).

Synthesis Example 9

Synthesis of tri(4,5-epoxypentyl)-1,2,4-cyclohexanetricarboxylic acid ester

To a reactor equipped with a Dean-Stark apparatus and a condenser, 13 g of 1,2,4-cyclohexanetricarboxylic acid, 1 g of p-toluenesulfonic acid monohydrate, 150 mL of toluene, and 19 g of 4-penten-1-ol were charged, and the mixture was caused to react at a reflux temperature for 8 hours. After completion of the reaction, the mixture was washed with sodium bicarbonate water and washed with water, and then concentrated to obtain 26 g of tri(4-pentenyl)-1,2,4-cyclohexanetricarboxylic acid ester as a colorless liquid.

H-NMR (300 MHz, CDCl₃): δ=5.84-5.74 (m, 3H), 5.07-4.97 (m, 6H), 4.13-4.06 (m, 6H), 3.26-3.25 (m, 1H), 2.45-1.67 (m, 20H),

LC-MS (ESI): m/z=420.5 (M+H).

To a reactor, 25 g of tri(4-pentenyl)-1,2,4-cyclohexanetricarboxylic acid ester and 500 ml of chloroform were charged, and the mixture was cooled to 0° C. to 10° C. Thereafter, 50 g of m-chloroperbenzoic acid was added and a temperature of the mixture was raised to room temperature and the mixture was caused to react for 23 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=30:70→0:100) to obtain 27 g of a light yellow liquid.

The obtained compound was tri(4,5-epoxypentyl)-1,2,4-cyclohexanetricarboxylic acid ester corresponding to Formula (1-14). The viscosity was 423 mPa·s at 25° C. This epoxy compound was determined as (i-9).

H-NMR (300 MHz, CDCl₃): δ=4.17-4.12 (m, 6H), 3.23 (m, 1H), 2.96-2.90 (m, 3H), 2.78-2.75 (m, 3H), 2.45-2.44 (m, 4H), 2.34-2.28 (m, 3H), 2.03-1.38 (m, 16H),

LC-MS (ESI): m/z=491.3 (M+Na).

Synthesis Example 10

Synthesis of tri(3,4-epoxybutyl)-1,2,4-cyclohexanetricarboxylic acid ester

To a reactor equipped with a Dean-Stark apparatus and a condenser, 13 g of 1,2,4-cyclohexanetricarboxylic acid, 1 g of p-toluenesulfonic acid monohydrate, 150 mL of toluene, and 16 g of 3-buten-1-ol were charged, and the mixture was caused to react at a reflux temperature for 4 hours. After completion of the reaction, the mixture was washed with sodium bicarbonate water and washed with water, and then concentrated to obtain 22 g of tri(3-butenyl)-1,2,4-cyclohexanetricarboxylic acid ester as a colorless liquid.

H-NMR (300 MHz, CDCl₃): δ=5.82-5.71 (m, 3H), 5.14-5.05 (m, 6H), 4.19-4.10 (m, 6H), 4.09 (m, 1H), 3.24-2.26 (m, 11H), 1.99-1.83 (m, 2H), 1.47-1.38 (m, 1H),

LC-MS (ESI): m/z=401.2 (M+Na).

To a reactor, 22 g of tri(3-butenyl)-1,2,4-cyclohexanetricarboxylic acid ester and 500 ml of chloroform were charged, and the mixture was cooled to 0° C. to 10° C. Thereafter, 47 g of m-chloroperbenzoic acid was added and a temperature of the mixture was raised to room temperature and the mixture was caused to react for 90 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=50:50→0:100) to obtain 22 g of a colorless liquid.

The obtained compound was tri(3,4-epoxybutyl)-1,2,4-cyclohexanetricarboxylic acid ester corresponding to Formula (1-13). The viscosity was 568 mPa·s at 25° C. This epoxy compound was determined as (i-10).

H-NMR (300 MHz, CDCl₃): δ=4.28-4.22 (m, 6H), 3.28 (m, 1H), 2.99 (m, 3H), 2.81-2.78 (m, 3H), 2.52-2.50 (m, 4H), 2.36-2.32 (m, 3H), 2.06-1.40 (m, 10H),

LC-MS (ESI): m/z=449.2 (M+Na).

Synthesis Example 11

Synthesis of tetra(4,5-epoxypentyl)-5-(2,5-dioxotetrahydrofuryl)-3-methyl-3,4-epoxycyclohexane-1,2-dicarboxylic acid ester To a reactor equipped with a Dean-Stark apparatus and a condenser, 10 g of 5-(2,5-dioxotetrahydrofuryl)-3-methyl-3-cyclohexene-1,2-dicarboxylic acid anhydride, 0.7 g of p-toluenesulfonic acid monohydrate, 100 mL of toluene, and 16 g of 4-penten-1-ol were charged, and the mixture was caused to react at a reflux temperature for 12 hours. After completion of the reaction, the mixture was washed with sodium bicarbonate water and washed with water, and then concentrated. The concentrated mixture was purified by silica gel chromatography (as a developing solvent, hexane:ethyl acetate was used in a volume ratio of hexane:ethyl acetate of 80:20) to obtain 21 g of tetra(4-pentenyl)-5-(2,5-dioxotetrahydrofuryl)-3-methyl-3-cyclohexene-1,2-dicarboxylic acid ester as a yellow liquid.

H-NMR (300 MHz, CDCl$_3$): δ=5.84-5.72 (m, 4H), 5.55 (m, 1H), 5.06-4.97 (m, 8H), 4.13-4.05 (m, 8H), 3.33-3.32 (s, 1H), 2.81-1.69 (m, 26H),

GC-MS (CI): m/z=574 (M+H).

To a reactor, 20 g of tetra(4-pentenyl)-5-(2,5-dioxotetrahydrofuryl)-3-methyl-3-cyclohexene-1,2-dicarboxylic acid ester and 300 ml of chloroform were charged, and the mixture was cooled to 0° C. to 10° C. Thereafter, 49 g of m-chloroperbenzoic acid was added and a temperature of the mixture was raised to room temperature and the mixture was caused to react for 24 hours. After completion of the reaction, the mixture was quenched with a sodium thiosulfate aqueous solution and sodium bicarbonate water was added to the mixture so that extraction was carried out. The organic phase was washed with water and dried and the solvent was evaporated to obtain a crude product. The crude product was purified by silica gel chromatography (as a developing solvent, hexane:ethyl acetate was used in a volume ratio of hexane:ethyl acetate=40:60→0:100) to obtain 22 g of a colorless liquid.

The obtained compound was tetra(4,5-epoxypentyl)-5-(2,5-dioxotetrahydrofuryl)-3-methyl-3,4-epoxycyclohexane-1,2-dicarboxylic acid ester corresponding to Formula (1-23). The viscosity was 4314 mPa·s at 25° C. This epoxy compound was determined as (i-11).

H-NMR (300 MHz, CDCl$_3$): δ=4.17-4.10 (m, 8H), 3.29-2.49 (m, 17H), 2.04-1.39 (m, 23H),

LC-MS (ESI): m/z=675.6 (M+Na).

Synthesis Example 12

Synthesis of tetra(4,5-epoxypentyl)-2,3,5,6-bicyclo[2.2.2]7-octenetetracarboxylic acid ester To a reactor equipped with a Dean-Stark apparatus and a condenser, 12 g of bicyclo[2.2.2]7-octene-2,3,5,6-tetracarboxylic acid dianhydride, 0.5 g of p-toluenesulfonic acid monohydrate, 100 mL of toluene, and 18 g of 4-penten-1-ol were charged, and the mixture was caused to react at a reflux temperature for 19 hours. After completion of the reaction, the mixture was washed with sodium bicarbonate water and washed with water, and then concentrated. The concentrated mixture was purified by silica gel chromatography (as a developing solvent, hexane:ethyl acetate was used in a volume ratio of hexane:ethyl acetate=90:10→70:30) to obtain 25 g of tetra(4-pentenyl)-2,3,5,6-bicyclo[2.2.2]7-octenetetracarboxylic acid ester as white solid.

H-NMR (300 MHz, CDCl$_3$): δ=6.38-6.35 (m, 2H), 5.83-5.71 (m, 4H), 5.06-4.96 (m, 8H), 4.09-3.93 (m, 8H), 3.33 (s, 2H), 3.05 (s, 4H), 2.13-2.05 (m, 8H), 1.73-1.64 (m, 8H),

LC-MS (ESI): m/z=557.5 (M+H).

To a reactor, 24 g of tetra(4-pentenyl)-2,3,5,6-bicyclo[2.2.2]7-octenetetracarboxylic acid ester and 500 ml of chloroform were charged, and the mixture was cooled to 0 C to 10° C. Thereafter, 60 g of m-chloroperbenzoic acid was added and a temperature of the mixture was raised to room temperature and the mixture was caused to react for 23 hours. After completion of the reaction, the mixture was quenched with a sodium thiosulfate aqueous solution and sodium bicarbonate water was added to the mixture so that extraction was carried out. The organic phase was washed with water and dried and the solvent was evaporated to obtain a crude product. The crude product was purified by silica gel chromatography (as a developing solvent, hexane:ethyl acetate was used in a volume ratio of hexane:ethyl acetate=20:80→0:100) to obtain 25 g of a light yellow liquid.

The obtained compound was tetra(4,5-epoxypentyl)-2,3,5,6-bicyclo[2.2.2]7-octenetetracarboxylic acid ester corresponding to Formula (1-26). The viscosity was 5901 mPa·s at 25° C. This epoxy compound was determined as (i-12).

H-NMR (300 MHz, CDCl$_3$): δ=6.37-6.34 (m, 2H), 4.13-3.99 (m, 8H), 3.32 (s, 2H), 3.04 (m, 4H), 2.95-2.89 (m, 4H), 2.77-2.74 (m, 4H), 2.49-2.47 (m, 4H), 1.80-1.51 (m, 16H),

LC-MS (ESI): m/z=621.5 (M+H).

Reference Example 1

Synthesis of tetra(2,3-epoxypropyl)-1,2,3,4-butanetetracarboxylic acid ester

To a reactor, 53 g of 1,2,3,4-butanetetracarboxylic acid, 155 g of potassium carbonate, 892 mL of N,N-dimethylformamide, and 177 g of allyl bromide were charged, and the mixture was caused to react at 68° C. for 11 hours. After completion of the reaction, the mixture was washed with water with toluene, and then concentrated. The concentrated mixture was purified by silica gel chromatography (as a developing solvent, hexane:ethyl acetate was used in a volume ratio of hexane:ethyl acetate of 80:20) to obtain 71 g of tetra(2-propenyl)-1,2,3,4-butanetetracarboxylic acid ester as a light yellow liquid.

H-NMR (300 MHz, CDCl$_3$): δ=5.94-5.82 (m, 4H), 5.35-5.22 (m, 8H), 4.61-4.58 (m, 8H), 3.41-3.37 (m, 2H), 2.90-2.81 (m, 2H), 2.50-2.43 (m, 2H),

GC-MS (CI): m/z=395 (M+H).

To a reactor, 40 g of tetra(2-propenyl)-1,2,3,4-butanetetracarboxylic acid ester and 800 mL of chloroform were charged, and the mixture was cooled to 0° C. to 10° C. Thereafter, 112 g of m-chloroperbenzoic acid was added and a temperature of the mixture was raised to room temperature and the mixture was caused to react for 96 hours. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate of 20:80) to obtain 22 g of a colorless liquid. When the colorless liquid was left at room temperature, a crystal was deposited, and thus, the crystal was washed with ethanol to obtain a white solid. A melting point of the crystal measured by DSC was 49.6° C.

The obtained compound was tetra(3,4-epoxypropyl)-1,2,3,4-butanetetracarboxylic acid ester corresponding to Formula (D-1). This epoxy compound was determined as (i-13).

H-NMR (300 MHz, CDCl$_3$): δ=4.52-4.42 (m, 4H), 4.00-3.90 (m, 4H), 3.44-3.41 (m, 2H), 3.25-3.18 (m, 4H), 2.93-2.83 (m, 6H), 2.67-2.63 (m, 4H), 2.55-2.49 (m, 2H),

LC-MS (ESI): m/z=481.2 (M+Na).

Formula (D-1)

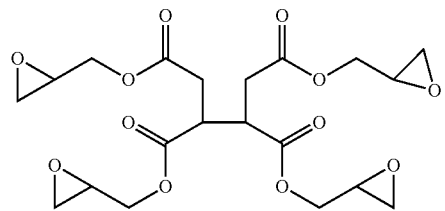

Reference Example 2

Synthesis of tri(2,3-epoxypropyl)-1,2,4-cyclohexanetricarboxylic acid ester

To a reactor, 20 g of 1,2,4-cyclohexanetricarboxylic acid, 500 mL of dimethylformamide, 51 g of potassium carbonate, and 50 g of allyl bromide were charged, and the mixture was caused to react at 65° C. for 4 hours. After completion of the reaction, a solid was filtered and washed with toluene. The obtained organic phase was washed with water and the solvent was evaporated to obtain 32 g of tri(2-propenyl)-1,2,4-cyclohexanetricarboxylie acid ester as a yellow liquid.

H-NMR (300 MHz, CDCl$_3$): δ=5.95-5.83 (m, 3H), 5.33-5.19 (m, 6H), 4.60-4.56 (m, 6H), 3.29 (s, 1H), 2.54-1.53 (m, 8H),

LC-MS (ESI): m/z=359.2 (M+Na).

To a reactor, 30 g of tri(2-propenyl)-1,2,4-cyclohexanetricarboxylic acid ester and 500 ml of chloroform were charged, and the mixture was cooled to 0° C. to 10° C. Thereafter, 74 g of m-chloroperbenzoic acid was added and a temperature of the mixture was raised to room temperature and the mixture was caused to react for 5 days. After completion of the reaction, the mixture was quenched with a sodium thiosulfate aqueous solution and sodium bicarbonate water was added to the mixture so that extraction was carried out. The organic phase was washed with water and the solvent was evaporated to obtain a crude product. The crude product was purified by silica gel chromatography (as a developing solvent, hexane:ethyl acetate was used in a volume ratio of hexane:ethyl acetate=50:50→10:90) to obtain 25 g of a colorless liquid.

The obtained compound was tri(2,3-epoxypropyl)-1,2,4-cyclohexanetricarboxylic acid ester corresponding to Formula (D-2). The viscosity was 2509 mPa·s at 25° C. This epoxy compound was determined as (i-14).

H-NMR (300 MHz, CDCl$_3$): δ=4.48-4.38 (m, 3H), 3.96-3.88 (m, 3H), 3.33 (s, 1H), 3.22-3.18 (m, 3H), 2.86-2.81 (m, 3H), 2.65-2.63 (m, 3H), 2.62-1.53 (m, 8H),

LC-MS (ESI): m/z=385.2 (M+H).

Formula (D-2)

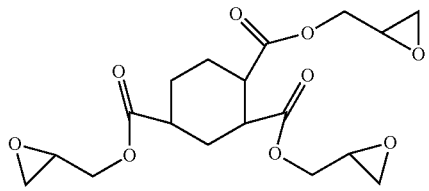

[Preparation of Heat-Cured Product]

Example 1

To a reactor, 16.8 g of the epoxy compound (i-1) and 17.5 g of acid anhydride curing agent Rikacid MH-700 (trade name, manufactured by New Japan Chemical Co., Ltd., its component is a mixture of 4-methylhexahydrophthalic anhydride and hexahydrophthalic anhydride in a molar ratio of 70:30) were charged, and the mixture was defoamed with stirring at room temperature for 30 minutes under reduced pressure. As a curing accelerator, 0.17 g of Hishicolin PX-4ET (trade name, manufactured by The Nippon Synthetic Chemical Industry Co., Ltd., its component is tetrabutylphosphonium diethylphosphorodithioate) was added, and the mixture was further defoamed with stirring for 5 minutes. This mixture was poured into a gap between release agent-treated glass plates (the treatment was carried out at 150° C. for 1 hour using a release agent SR-2410 (trade name) manufactured by Dow Corning Toray Co., Ltd.) sandwiching a silicone rubber having a thickness of 3 mm. The cured product was obtained by carrying out pre-curing at 100° C. for 2 hours and curing at 150° C. for 5 hours.

Example 2

Similar to Example 1, 25.0 g of the epoxy compound (i-2), 28.5 g of Rikacid MH-700, and 0.25 g of Hishicolin PX-4ET were charged and a cured product was obtained.

Example 3

Similar to Example 1, 12.6 g of the epoxy compound (i-3), 16.0 g of Rikacid MH-700, and 0.12 g of Hishicolin PX-4ET were charged and a cured product was obtained.

Example 4

Similar to Example 1, 18.0 g of the epoxy compound (i-4), 20.6 g of Rikacid MH-700, and 0.18 g of Hishicolin PX-4ET were charged and a cured product was obtained.

Example 5

Similar to Example 1, 17.2 g of the epoxy compound (i-5), 19.3 g of Rikacid MH-700, and 0.17 g of Hishicolin PX-4ET were charged and a cured product was obtained.

Example 6

Similar to Example 1, 16.8 g of the epoxy compound (i-6), 16.2 g of Rikacid MH-700, and 0.17 g of Hishicolin PX-4ET were charged and a cured product was obtained.

Example 7

Similar to Example 1, 16.3 g of the epoxy compound (i-7), 17.1 g of Rikacid MH-700, and 0.17 g of Hishicolin PX-4ET were charged and a cured product was obtained.

Example 8

Similar to Example 1, 18.4 g of the epoxy compound (i-8), 17.7 g of Rikacid MH-700, and 0.18 g of Hishicolin PX-4ET were charged and a cured product was obtained.

Example 9

Similar to Example 1, 18.2 g of the epoxy compound (i-9), 19.1 g of Rikacid MH-700, and 0.18 g of Hishicolin PX-4ET were charged and a cured product was obtained.

Example 10

Similar to Example 1, 14.6 g of the epoxy compound (i-10), 16.8 g of Rikacid MH-700, and 0.17 g of Hishicolin PX-4ET were charged and a cured product was obtained.

Example 11

Similar to Example 1, 16.1 g of the epoxy compound (i-11), 20.2 g of Rikacid MH-700, and 0.16 g of Hishicolin PX-4ET were charged and a cured product was obtained.

Example 12

Similar to Example 1, 19.3 g of the epoxy compound (i-12), 20.3 g of Rikacid MH-700, and 0.19 g of Hishicolin PX-4ET were charged and a cured product was obtained.

Comparative Example 1

Similar to Example 1, 14.6 g of the epoxy compound (i-13), 20.9 g of Rikacid MH-700, and 0.15 g of Hishicolin PX-4ET were charged and a cured product was obtained.

Comparative Example 2

Similar to Example 1, 19.8 g of the epoxy compound (i-14), 25.3 g of Rikacid MH-700, and 0.20 g of Hishicolin PX-4ET were charged and a cured product was obtained.

A three-point bending test (bending strength and bending modulus), transmittance, linear expansion coefficient, and glass-transition temperature were measured for the obtained cured products.

(Measurement of Bending Properties)

The bending properties were measured based on JIS K-6911 using a tensile tester. A height and a width of a specimen were measured. The specimen was held, and a load was applied to the center of the specimen with a pressure wedge. A load at the time of break of the specimen was measured and the bending strength (G) was calculated.

Followings are determined:
Bending strength σ: (MPa) {kgf/mm$^2$}
P: Load at the time of break of specimen (N) {kgf}
L: Distance between support points (mm)
W: Width of specimen (mm)
h: Height of specimen (mm)

$$\sigma = (3PL)/(2Wh^2)$$

Bending modulus (E):(MPa) {kgf/mm$^2$} can be calculated by the following formula where F/Y (N/mm) {kgf/mm} is a slope of a linear part of the load-deflection curve, $$E = [(L^3/4Wh^3)] \times [F/Y]$$

(Measurement of Transmittance)

The transmittance at 400 nm was measured using a spectrophotometer.

(Measurement of Linear Expansion Coefficient)

Measurement of the linear expansion coefficient was measured based on JIS K-6911.

A thickness of the specimen was precisely measured and the linear expansion coefficient was measured by an expansion/compression method under a load of 0.05 N and at a temperature rise rate of 5° C./minute using TMA (thermo mechanical analysis).

The Linear expansion coefficient α1 was calculated based on the following formula:

Variation of length between 30° C. to 80° C. (ΔL1)/ Initial length of specimen (L)×50=α1.

(Measurement of Glass-Transition Temperature (Tg))

A thickness of the specimen was precisely measured and the linear expansion coefficient was measured by an expansion/compression method under a load of 0.05 N and at a temperature rise rate of 5° C./minute using TMA. Tangential lines of the curves before and after the glass-transition point were drawn and Tg was found at the intersection point of these tangential lines.

(Measurement of Boiling Water Absorption)

The boiling water absorption was measured based on JIS K-6911. Drying treatment of a specimen was carried out for 24 hours in a thermostatic oven in which the temperature was maintained at 50° C. After the treatment, the specimen was cooled in a desiccator to 20° C. and the mass of the specimen was measured. The specimen was immersed in boiling distilled water and boiled for 100 hours. Thereafter, the specimen was removed and cooled in running water of 20° C. for 30 minutes. After the attached water was wiped out, a mass of the specimen after the water absorption was immediately measured.

A: Boiling water absorption (%), $W_1$: Mass of specimen before boiling (g), $W_2$: Mass of specimen after boiling (g).

The boiling water absorption was calculated based on the following formula.

$$A = [(W_2 - W_1)/W_1] \times 100$$

TABLE 1

| | Bending strength MPa | Bending modulus MPa | Transmittance % | Tg ° C. | Linear expansion coefficient ppm/° C. |
|---|---|---|---|---|---|
| Example 1 | 135 | 2674 | 75 | 115 | 95 |
| Example 2 | 154 | 2969 | 76 | 128 | 91 |
| Example 3 | 178 | 3497 | 84 | 150 | 77 |
| Example 4 | 161 | 3109 | 81 | 122 | 89 |
| Example 5 | 147 | 2748 | 78 | 155 | 89 |
| Example 6 | 137 | 2614 | 79 | 103 | 104 |
| Example 7 | 153 | 2830 | 83 | 135 | 90 |
| Example 8 | 141 | 2737 | 69 | 105 | 100 |
| Example 9 | 149 | 3457 | 81 | 95 | 93 |
| Example 10 | — | — | 84 | 104 | 86 |
| Example 11 | 140 | 3292 | 53 | 128 | 78 |
| Example 12 | 130 | 2993 | 70 | 167 | 84 |
| Comparative Example 1 | 158 | 3972 | 83 | 171 | 73 |
| Comparative Example 2 | 176 | 3617 | 86 | 172 | 72 |

From the results described above, it has been found that the curable resin composition of the present invention has sufficient heat curing performance even when the alkylene group between the oxygen atom of the ester group and the epoxy ring becomes longer in the epoxy ester of the carboxylic acid.

[Preparation of Photo Acid Generator]

A propylene carbonate solution of a sulfonium salt (Formula (B-2), active ingredient 50%, trade name CPI-101A, manufactured by San-Apro Ltd.) was prepared. This is determined as a photo acid generator (ii-1).

[Photo Curability Test of Curable Composition]

The epoxy compound and the photo acid generator were formulated, mixed at 40° C., and defoamed to prepare a curable composition. From Table 2 to Table 5, all formulation amounts were listed in parts by mass, and for the epoxy compounds and the photo acid generator, the active ingredients thereof were listed in parts by mass. The photo acid generator (ii-1) that is the propylene carbonate solution itself was used.

The prepared curable composition was irradiated with UV (ultraviolet) away from a distance of 9.5 cm. Photocuring behavior was observed by a rheometer (a viscometer). A time (seconds) at which a storage elastic modulus was reached to 10 to the fourth power Pa (1×10$^4$ Pa) was defined as the curing time (sec). The UV irradiation was carried out to 1200 seconds.

A rheometer manufactured by REOLOGICA Instruments (trade name VAR-50) was used as the rheometer, and an Hg—Xe lamp was used as the lamp. The UV irradiation was carried out in a wavelength of radiated UV of 365 nm and an amount of irradiation of 20 mW/cm². As an irradiation window material in the UV irradiation, a hard glass having a thickness of 3 mm was used. A film thickness of the coating film formed from the curable composition was 50 μm. A photo curing rate of the curable composition was measured.

TABLE 2

| Component | Example 13 | Example 14 | Example 15 | Comparative Example 3 |
|---|---|---|---|---|
| (i-1) | 100 | | | |
| (i-2) | | 100 | | |
| (i-3) | | | 100 | |
| (i-13) | | | | 100 |
| (ii-1) | 2 | 2 | 2 | 2 |
| Curing time (Second) | 10 | 21 | 391 | 562 |

TABLE 3

| Component | Example 16 | Example 17 | Example 18 | Example 19 |
|---|---|---|---|---|
| (i-4) | 100 | | | |
| (i-5) | | 100 | | |
| (i-6) | | | 100 | |
| (i-7) | | | | 100 |
| (ii-1) | 2 | 2 | 2 | 2 |
| Curing time (Second) | 21 | 47 | 16 | 21 |

TABLE 4

| Component | Example 20 | Example 21 | Example 22 | Comparative Example 4 |
|---|---|---|---|---|
| (i-8) | 100 | | | |
| (i-9) | | 100 | | |
| (i-10) | | | 100 | |
| (i-14) | | | | 100 |
| (ii-1) | 2 | 2 | 2 | 2 |
| Curing time (Second) | 30 | 31 | 1000 | Not cured |

TABLE 5

| Component | Example 20 | Example 21 |
|---|---|---|
| (i-11) | 100 | |
| (i-12) | | 100 |
| (ii-1) | 2 | 2 |
| Curing time (Second) | 60 | 75 |

From the results described above, it has been found that, in the curable composition of the present invention, photo curability is improved in proportion to an increase in length of the alkylene group between the oxygen atom of the ester group and the epoxy ring in the epoxy ester of the carboxylic acid.

INDUSTRIAL APPLICABILITY

The curable composition using the epoxy compound of the present invention has characteristics such as the low viscosity and the rapid curing and is applicable for coating and adhesion of electronic parts, optical parts, and precision mechanism parts. The curable composition can be used for, for example, adhesion of lenses for cellular phones and cameras, optical elements such as light emission diodes (LEDs) and laser diodes (LDs), liquid crystal panels, biochips, components of cameras, such as lenses and prisms, magnetic parts for hard disc drives for personal computers and the like, pick-ups (parts inputting optical information reflected from a disk) for CD and DVD players, cones and coils of speakers, magnets of motors, circuit boards, electronic parts, and parts in engines for automobiles and the like.

For hard coating materials for surface protection of automobile bodies, lamps, electric appliances, building materials, plastics, and the like, the curable composition is applicable for bodies of automobiles and motorcycles, mirrors and lenses of headlights, plastic lenses of glasses, cellular phones, game consoles, optical films, ID cards, and the like.

For ink materials for printing metals such as aluminum, plastics, and the like, applications of the curable composition include printing inks used for cards such as credit cards and membership cards, switches and keyboards of electric appliances and office automation equipment, and inks for ink-jet printers for CD, DVD, and the like.

Applications of the curable composition of the present invention also include a technique for producing complex three-dimensional objects by curing a resin in combination with three-dimensional CAD, applications for photo fabrication such as model production of industrial products, coating for optical fibers, adhesion, light guides, and thick film resists (for MEMS).

The invention claimed is:

1. A curable composition, comprising an epoxy compound of Formula (1):

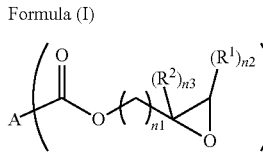

Formula (I)

wherein Formula (1), A is an (n4)-valent $C_{4-20}$ linear hydrocarbon group optionally containing an epoxy group, an (n4)-valent $C_{4-20}$ cyclic hydrocarbon group optionally containing an epoxy group, or an (n4)-valent group of a combination of the linear hydrocarbon group and the cyclic hydrocarbon group; $R^1$ and $R^2$ are each independently a hydrogen atom or a $C_{1-10}$ alkyl group; n1 is an integer of 2 to 6; n2 is an integer of 2; n3 is an integer of 1; and n4 is an integer of 3 to 8, wherein the curable composition further comprises a curing agent.

2. The curable composition according to claim 1, wherein A is an (n4)-valent organic group formed by removing (n4) hydrogen atoms from butane, pentane, or hexane.

3. The curable composition according to claim 1, wherein A is an (n4)-valent organic group formed by removing (n4) hydrogen atoms from cyclobutane, cyclopentane, cyclohexane, epoxycyclohexane, alkyl-substituted epoxycyclohexane, bicycloheptene, or bicyclooctene.

4. The curable composition according to claim 1, wherein the curing agent is at least one selected from the group consisting of an acid anhydride, amines, a phenol resin, a polyamide resin, imidazoles, and a polymercaptan.

5. The curable composition according to claim 1, wherein the curing agent is contained in a ratio of 0.5 equivalents to 1.5 equivalents relative to 1 equivalent of the epoxy group in the epoxy compound.

6. The curable composition according to claim 1, further comprising:
an acid generator.

7. The curable composition according to claim 6, wherein the acid generator is a photo acid generator or a thermal acid generator.

8. The curable composition according to claim 6, wherein the acid generator is an onium salt.

9. The curable composition according to claim 6, wherein the acid generator is a sulfonium salt compound or an iodonium salt compound.

10. The curable composition according to claim 6, wherein the acid generator is contained in a ratio of 0.1% by mass to 20% by mass per mass of the epoxy compound.

* * * * *